United States Patent [19]

Bodor

[11] Patent Number: 5,135,926
[45] Date of Patent: Aug. 4, 1992

[54] SOFT β-ADRENERGIC BLOCKING AGENTS

[76] Inventor: Nicholas S. Bodor, 6219 SW. 93rd Ave., Gainesville, Fla. 32608

[21] Appl. No.: 692,260

[22] Filed: Apr. 26, 1991

Related U.S. Application Data

[60] Continuation of Ser. No. 286,879, Dec. 20, 1988, abandoned, which is a division of Ser. No. 922,462, Oct. 23, 1986, Pat. No. 4,829,086, which is a continuation of Ser. No. 741,846, Jun. 6, 1985, abandoned, which is a continuation-in-part of Ser. No. 589,359, Mar. 14, 1984, abandoned.

[30] Foreign Application Priority Data

Mar. 13, 1985 [CA] Canada .................................. 476391

[51] Int. Cl.$^5$ ..................... C07C 229/00; A61K 31/55
[52] U.S. Cl. .................................. 514/211; 514/212;
514/218; 514/222.2; 514/226.8; 514/227.5;
514/228.8; 514/237.5; 514/255; 514/256;
514/330; 514/365; 514/372; 514/374; 514/378;
514/385; 514/403; 514/423; 514/539; 514/540;
540/544; 540/553; 540/575; 540/607; 544/3;
544/54; 544/58.4; 544/63; 544/162; 544/224;
544/335; 544/391; 546/226; 548/200; 548/214;
548/215; 548/240; 548/300; 548/356; 548/379;
548/540; 560/42
[58] Field of Search .................. 560/42; 540/544, 575,
540/553, 607; 544/3, 54, 58.4, 63, 88, 162, 224,
335, 391; 546/226; 548/200, 214, 215, 240, 300,
356, 379, 540; 514/211, 212, 218, 222.2, 226.8,
227.5, 228.8, 232.5, 255, 256, 330, 365, 372, 374,
378, 385, 403, 423, 539, 540

[56] References Cited

U.S. PATENT DOCUMENTS

| | | | |
|---|---|---|---|
| 3,663,607 | 5/1972 | Barrett et al. | 260/501.1 |
| 3,836,671 | 9/1974 | Barrett et al. | 424/324 |
| 4,387,103 | 6/1983 | Erhardt et al. | 424/309 |
| 4,454,154 | 6/1984 | Matier | 424/309 |
| 4,578,403 | 3/1986 | Matier | 514/522 |

FOREIGN PATENT DOCUMENTS

| | | |
|---|---|---|
| 0041491 | 12/1981 | European Pat. Off. . |
| 59-118746 | 7/1984 | Japan . |
| WO8201869 | 6/1982 | PCT Int'l Appl. . |
| WO8301772 | 5/1983 | PCT Int'l Appl. . |

OTHER PUBLICATIONS

Bodor et al, *Pharmaceutical Research*, 1984, No. 3, 120–125.

Erhardt et al, *J. Med. Chem.*, 1982, vol. 25, No. 12, 1408–1412.

*Primary Examiner*—Bruce Gray
*Attorney, Agent, or Firm*—Burns, Doane, Swecker & Mathis

[57] ABSTRACT

New soft β-adrenergic blocking agents, useful in the treatment or prevention of cardiovascular disorders and in the treatment of glaucoma, have the formula

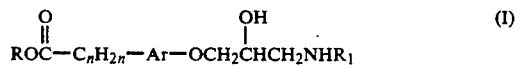

wherein n is an integer from 0 to 10; R is $C_6$–$C_{12}$ cycloalkyl-$C_pH_{2p}$-, $C_6$–$C_{18}$ polycycloalkyl-$C_pH_{2p}$-, $C_6$–$C_{18}$ polycycloalkenyl-$C_pH_{2p}$- or $C_6$–$C_{12}$ cycloalkenyl-$C_pH_{2p}$- (wherein p is 0, 1, 2 or 3), or together with the adjacent

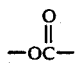

group represents a variety of other complex ester groupings; $R_1$ is $C_1$–$C_7$ alkyl; and Ar is a divalent radical containing at least one aromatic nucleus. The corresponding pharmaceutically acceptable acid addition salts are also described.

16 Claims, 4 Drawing Sheets

SOFT β-ADRENERGIC BLOCKING AGENTS

CROSS-REFERENCE TO RELATED APPLICATION

This application is a continuation of application Ser. No. 07/286,879, filed Dec. 20, 1988 now abandoned which is a division of application Ser. No. 6/922,462 filed Oct. 23, 1986 now U.S. Pat. No. 4,829,076 which is a continuation of application Ser. No. 6/731,846 filed Jun. 6, 1985 now abandoned which continuation-in-part of my earlier copending application Ser. No. 589,359, filed Mar. 14, 1984, now abandoned incorporated by reference herein in its entirety and relied upon.

FIELD OF THE INVENTION

The present invention provides novel compounds containing at least one aromatic nucleus which are soft β-adrenergic blocking agents, useful in the treatment or prevention of cardiovascular disorders and in the treatment of glaucoma.

BACKGROUND OF THE INVENTION

Many β-adrenergic blocking agents are known and used; unfortunately, however, these agents are generally subject to facile oxidative metabolic degradations. Many of the metabolites also possess significant β-blocking activity and, due to their different pharmacokinetic properties, make dosing and optimization of therapy difficult. The metabolites of bufuralol, for example, have longer biological half-lives than the parent drug. Francis et al, Biomed. Mass. Spectrometry, 3, 281–2854 (1976). Consequently, it is difficult to determine an adequate dose of the known β-blockers for administration, especially when administering them therapeutically to patients suffering from angina pectoris, hypertension or unexpected arrhythmias during surgical operations. It would be most desirable to design β-blockers which would be metabolized in a simple, predictable and controllable manner in one step to an inactive metabolite, regardless of the conditions of the patient and other drugs used. This would necessitate, however, avoiding oxidative metabolism.

The present inventor has previously devised a general soft drug approach having such objectives, one specific aspect of that approach being the inactive metabolite method. Bodor, in Proceedings of the 2nd IUPAC-IUPHAR Symposium on Strategy in Drug Research, Noordwijkerhout, J. A. Keverling Buisman (ed.), Elsevier Scientific Publishing Company, Amsterdam, 1982; Bodor, Belgian Patent No. 889,563, Nov. 3, 1981; Chem. Abstr. 97:6651n (1982). The principles of the inactive metabolite approach are:

(1) Start the design process with a known inactive metabolite of a drug.

(2) Alter the metabolite to obtain a structure that resembles (isosteric and/or isoelectronic) the starting or an analogous drug.

(3) Design the structure and metabolism of the new soft compound in such a way as to yield the starting inactive metabolite in one step without going through toxic intermediates.

(4) Control transport and binding properties as well as the rate of metabolism and pharmacokinetics by molecular manipulations in the activation stage. However, it is not necessary to wait for an inactive metabolite to be isolated; it may be possible to design the inactive metabolite during the general drug design process based on knowledge of structural requirements for activity as well as elimination and enzymatic cleavage.

Recently, several patent publications have described various series of short acting β-adrenergic blocking compounds containing ester moieties which are structurally related to some of the compounds of the present invention. Thus, Matier U.S. Pat. No. 4,454,154, issued Jun. 12, 1984, describes a method of treating glaucoma by topical administration of selected β-blockers. Lower alkyl ($C_1$–$C_{10}$) and lower cycloalkyl ($C_3$–$C_5$) esters are among the compounds generically disclosed by matier, but only alkyl esters are specifically described. See also related Erhardt et al U.S. Pat. No. 4,387,103, issued Jun. 7, 1983 and American Hospital Supply Corporation's corresponding International Application No. PCT/US81/01514 published under International Publication No. W082/01869 on Jun. 10, 1982; again, lower alkyl and lower cycloalkyl esters are generically disclosed, but of these only the lower alkyl esters are specifically described. The Erhardt et al patent and its PCT counterpart provide a method for the treatment or prophylaxis of cardiac disorders. A related series of short acting β-blockers is described in Aktiebolaget Hassle's European Patent Application No. 81850095.1, published on Dec. 9, 1981 under European Publication No. 0041491. The Hassle application generically discloses lower alkyl ($C_1$–$C_7$) and lower cycloalkyl ($C_3$–$C_6$) esters, among others, but again does not specifically describe any cycloalkyl esters. Moreover, none of these publications appear to address the problem addressed by the present invention, i.e. how to design β-blockers which would be metabolizes in one simple, predictable, controllable step to an inactive metabolite which avoiding oxidative metabolism; moreover, the esters of the publications are generally less complex structurally than those described hereinbelow. See also Erhardt et al, J. Med. Chem., 25, 1408–1412 (1982). Similar simple alkyl esters were described much earlier, e.g. Barrett et al U.S. Pat. No. 3,663,607, issued May 16, 1972.

SUMMARY AND OBJECTS OF THE INVENTION

In view of the foregoing, it is an object of this invention to provide a new class of β-adrenergic agents which will be metabolized in a simple, predictable and controllable manner in one step to an inactive metabolite. It is another object of the present invention to provide new β-adrenergic agents which are not subject to significant oxidative metabolism. It is another object of this invention to apply the present inventor's general inactive metabolite approach to the design of novel soft β-blockers.

These and other objects of the present invention are achieved by providing compounds of the formula

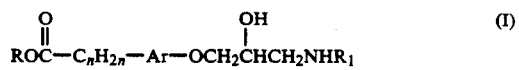

$$ROC-C_nH_{2n}-Ar-OCH_2CHCH_2NHR_1 \quad (I)$$

wherein:

n is an integer from 0 to 10 inclusive;

R is (1) $C_6$–$C_{12}$cycloalkyl-$C_pH_{2p}$- wherein p is 0, 1, 2 or 3; (2) $C_6$–$C_{18}$ polycycloalkyl-$C_pH_{2p}$- wherein p is defined as above; (3) $C_6$–$C_{18}$ polycycloalkenyl-$C_pH_{2p}$- wherein p is defined as above; (4) $C_6$–$C_{12}$ cycloalkenyl-$C_pH_{2p}$ wherein p is defined as above;

(5) —CH$_2$—X—R$_2$ wherein X is S, SO or SO$_2$ and R$_2$ is C$_1$-C$_7$ alkyl or C$_3$-C$_{12}$ cycloalkyl; (6)

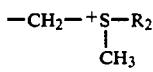

wherein R$_2$ is defined as above; (7)

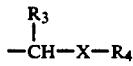

wherein X is defined as above, and wherein R$_3$ is C$_1$-C$_7$ alkyl and R$_4$ is C$_1$-C$_7$ alkyl or wherein R$_3$ and R$_4$ taken together represent —(CH$_2$)$_m$— wherein m is 3 or 4 and —(CH$_2$)$_m$— is optionally substituted by one to three C$_1$-C$_7$ alkyl; (8)

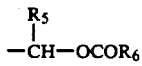

wherein R$_5$ is hydrogen or C$_1$-C$_7$ alkyl and R$_6$ is unsubstituted or substituted C$_1$-C$_7$ alkyl, C$_3$-C$_{12}$ cycloalkyl, C$_3$-C$_{12}$ cycloalkenyl or C$_2$-C$_8$ alkenyl, the substituents being selected from the group consisting of halo, C$_1$-C$_7$ alkoxy, C$_1$-C$_7$ alkylthio, C$_1$-C$_7$ alkylsulfinyl, C$_1$-C$_7$ alkylsulfonyl,

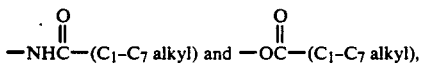

or R$_6$ is unsubstituted or substituted phenyl or benzyl, the substituents being selected from the group consisting of C$_1$-C$_7$ alkyl, C$_1$-C$_7$ alkoxy, halo, carbamoyl, C$_2$-C$_8$ alkoxycarbonyl, C$_2$-C$_8$ alkanoyloxy, C$_1$-C$_7$ haloalkyl, mono(C$_1$-C$_7$ alkyl)amino, di(C$_1$-C$_7$ alkyl)amino, mono(C$_1$-C$_7$ alkyl)carbamoyl, di(C$_1$-C$_7$ alkyl)carbamoyl, C$_1$-C$_7$ alkylthio, C$_1$-C$_7$ alkylsulfinyl and C$_1$-C$_7$ alkylsulfonyl; (9)

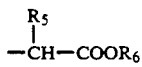

wherein R$_5$ and R$_6$ are defined as above; or (10)

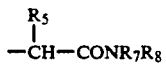

wherein R$_5$ is defined as above, and R$_7$ and R$_8$, which can be the same or different, are each hydrogen, C$_1$-C$_7$ alkyl, C$_3$-C$_{12}$ cycloalkyl, phenyl or benzyl, or R$_7$ and R$_8$ are combined such that —NR$_7$R$_8$ represents the residue of a saturated monocyclic secondary amine;

R$_1$ is C$_1$-C$_7$ alkyl;

and Ar is a divalent radical containing at least one aromatic nucleus.

The compounds of the present invention avoid the disadvantages of many known β-blockers resulting from their active metabolites. The compounds of formula (I) are rationally designed so that when administered to a mammal they are subjected to an enzymatic hydrolytic (i.e. esterase) process which is much faster than oxidative metabolism and which leads to hydrolyzed metabolites which possess very little or no β-adrenergic activity. Thus, for example, in the case of a group of preferred metoprolol derivatives of the invention, such are designed to hydrolytically deactivate to the phenylacetic acid derivative, i.e. the compound of the formula

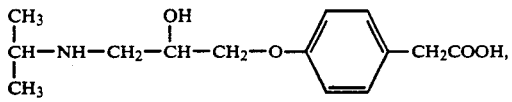

which is an inactive metabolite of metoprolol and the major metabolite found in the urine. [See, for example, Borg et al, Acta Pharmacol. Toxicol., 36 (Suppl. V), 125-135 (1975).] The rate of hydrolysis deactivation may be controlled by the structure of the esters.

Accordingly, the compounds of the present invention exhibit excellent β-blocking efficacy without adverse side effects for a certain duration, dependent only on the hydrolytic metabolism rate. As a consequence, it is easy to control and maintain adequate therapeutic action with a desirable onset time using the present compounds. The onset time is usually short compared with conventional β-adrenergic blocking agents; therefore, the instant compounds are expected to be of particular use in the treatment of arrhythmias, ischemic heart disease and hypertension, possibly attending surgical operations. The instant compounds are also expected to be of special value when used in the treatment of glaucoma, since they will not only reduce intraocular pressure when applied locally to the eye, but because of their "soft" nature will deactivate during absorption and thus avoid the typical β-blocker systemic side effects which attend use of known β-blockers for this purpose.

DETAILED DESCRIPTION OF THE INVENTION

Figure 1:
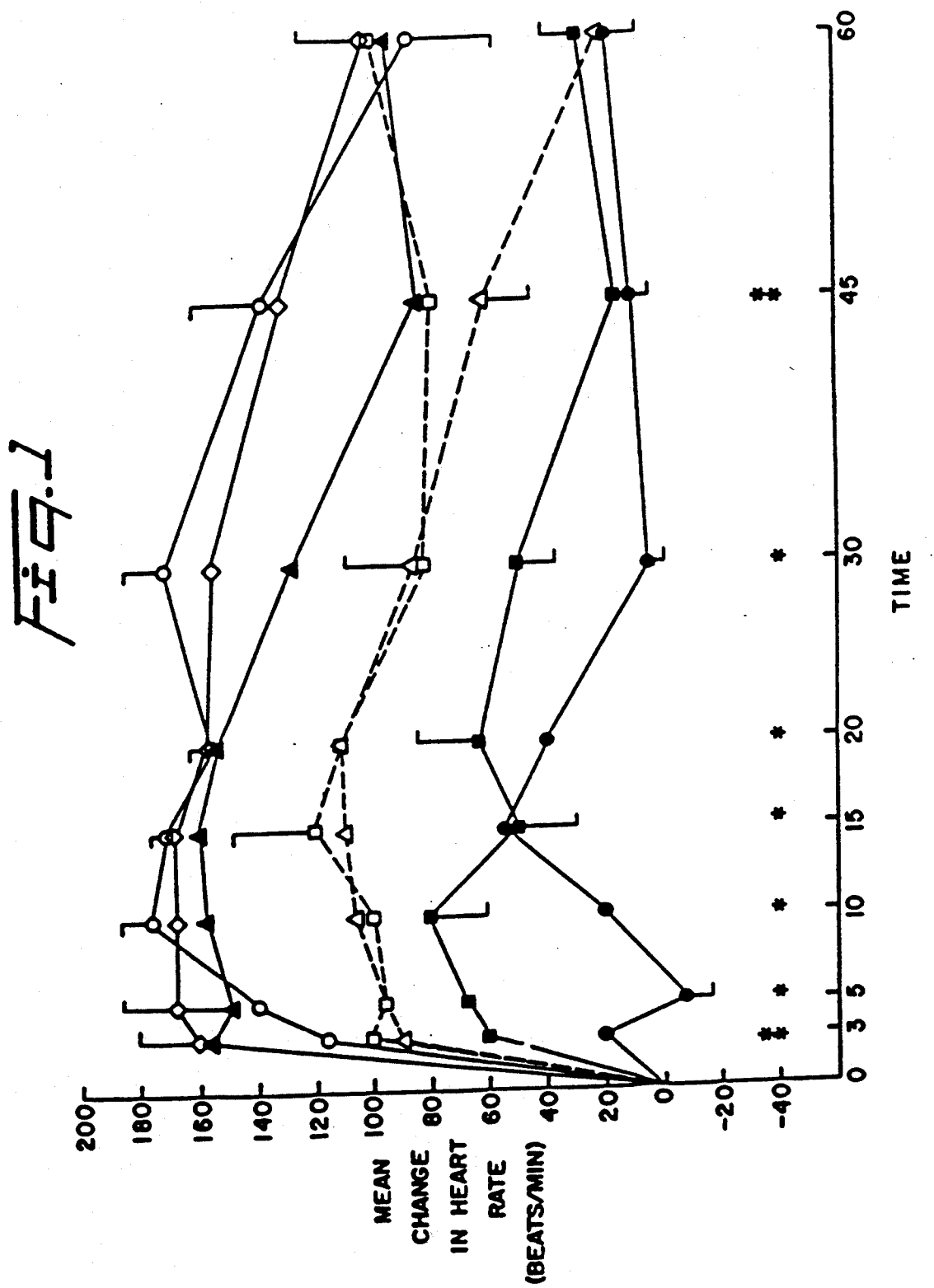
FIG. 1 is a graph plotting the mean change in heart rate (beats/minute) with time following subcutaneous administration of 25 μg/kg of isoproterenol to groups of rats pretreated 60 minutes prior to isoproterenol administration with 6 mg/kg of test compound or control vehicle.

With respect to the various groups encompassed by the generic terms used in this specification, the following definitions and explanations are applicable:

The divalent radicals containing at least one aromatic nucleus which are represented by Ar can be unsubstituted or substituted monocyclic or polycyclic ring systems and may include hetero ring atoms, particularly N and O. Illustrative divalent radicals represented by Ar include the following:

(1) phenylene, i.e. a radical of the formula

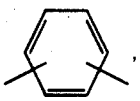

especially 1,4-phenylene and 1,3-phenylene, optionally bearing one or more substituents such as $C_1$-$C_7$ alkyl, e.g. $CH_3CH_2$- or $CH_3$-; $C_1$-$C_7$ alkyl—O—$C_1$-$C_7$ alkylene-, e.g. $CH_3OCH_2CH_2$-; $C_2$-$C_8$ alkenyl, e.g. $CH_2=CH—CH_2$-; $C_1$-$C_7$ alkyl—S—, e.g. $CH_3$—S—; $C_2$-$C_8$ alkenyl—O—, e.g. $CH_2CH=CH_2$—O—; $C_3$-$c_{12}$ cycloalkyl, e.g. cyclopentyl; $C_1$-$C_7$ alkyl—CONH—, e.g. $CH_3CH_2CH_2CONH$— or $CH_3CONH$—; $C_1$-$C_7$ alkyl—CO—, e.g. $CH_3CO$—; and/or $H_2NCO$—$C_1$-$C_7$ alkylene-; e.g. $H_2NCO$—$CH_2$—;

(2) divalent fused ring systems containing two or three rings, optionally containing one or two N, S or O ring atoms, such as:

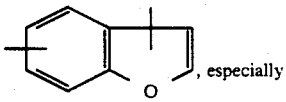, especially (a)

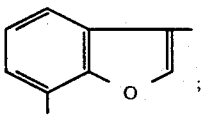; (b)

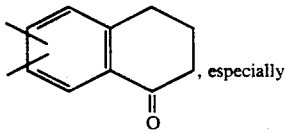, especially

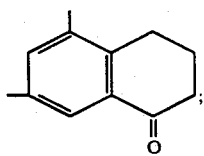; (c)

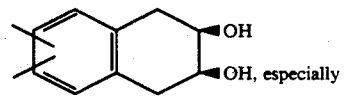, especially

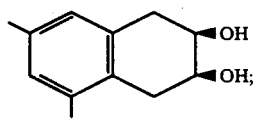

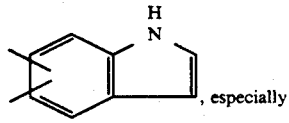

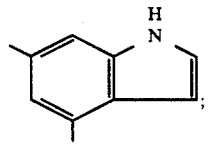, especially (d)

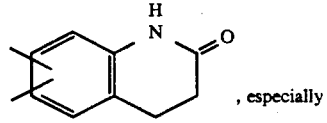

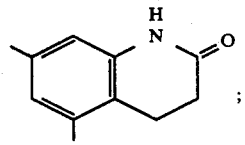, especially (e)

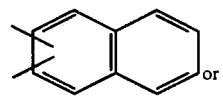;

and

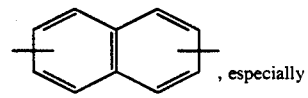or (f)

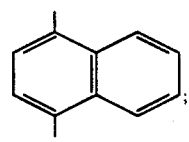, especially

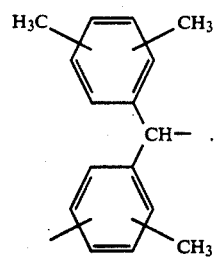;

and (3) divalent aryl-alkylene-aryl systems, e.g. phenylene-$C_1$-$C_3$ alkylene-phenyl radicals such as

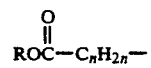

Preferably, the divalent radical represented by Ar is selected such that the $$\underset{\text{ROC}}{\overset{\text{O}}{\|}}—C_nH_{2n}—$$

grouping in formula (I) either simply replaces a hydrogen atom on the corresponding ring of a known β-blocker or replaces a noncritical ring substituent on the corresponding ring of a known β-blocker, e.g. a lower alkyl, lower alkyl-O-lower alkylene-, lower alkyl—CONH— or $H_2NCO$-lower alkylene- substituent. Particularly preferred compounds of the invention bear such a structural relationship to metoprolol, bufuralol, alprenolol, bunolol, xipranolol, nadolol, tiprenolol, oxprenolol, penbutolol, pindolol, carteolol, propranolol, acebutolol, atenolol and practolol. Analogues of metoprolol are especially preferred. It should be emphasized that the divalent radicals represented by Ar must contain at least one true aromatic nucleus, i.e. at least one benzene ring. Thus, a ring system such as

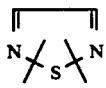

is not within the meaning of Ar as defined herein. Hetero atoms may be present, however, when located in a ring or rings fused or appended to a benzene ring, e.g. as in (2) (a), (d) and (e) above.

The alkyl, alkenyl and alkylene groupings encompassed by any of the structural variables in formula (I) can be straight or branched-chain groups containing the indicated number of carbon atoms. The term "lower" used in conjunction with such radicals indicates that they may contain up to 7 carbon atoms.

Specific examples of alkyl radicals encompassed by formula (I), whether as specific values for $R_1$ or as a portion of an R or Ar group, include methyl, ethyl, propyl, butyl, pentyl, hexyl and heptyl and their branched-chain isomers, e.g. isopropyl, isobutyl and tert-butyl. Preferred values for $R_1$ are isopropyl and tert-butyl.

The alkenyl radicals encompassed by various R and Ar values can be exemplified by vinyl, propenyl and butenyl and the branched-chain groups having 3 or more carbon atoms.

The alkylene moieties encompassed by $C_nH_{2n}$ when n is other than zero) as well as those encompassed by various values for R and Ar are typified by methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene and the like.

The alkoxy, alkylthio, alkylsulfinyl, alkylsulfonyl, alkoxycarbonyl, alkanoyloxy, monoalkylamino, dialkylamino, monoalkylcarbamoyl and dialkylcarbamoyl groupings are of the type —O-alkyl —S-alkyl —SO-alkyl —SO₂-alkyl

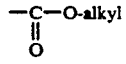

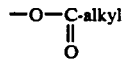

—NH-alkyl

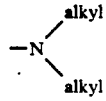

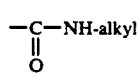

and

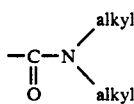

respectively, wherein alkyl is as hereinbefore defined and exemplified.

The halo substituents can be chloro, bromo, iodo or fluoro. The haloalkyl substituents can be monohaloalkyl or polyhaloalkyl, straight or branched-chain, substituted with from 1 to 3 halogen atoms, the term "halogen" as used herein including chlorine, bromine, iodine or fluorine. Specific examples of the contemplated monohaloalkyl and polyhaloalkyl groups include chloromethyl, dichloromethyl, trichloromethyl, bromomethyl, fluoromethyl, difluoromethyl, trifluoromethyl, 1-fluoroethyl, 1-chloroethyl, 2-chloroethyl, 2,2,2-trichloroethyl, 2,2,2-trifluoroethyl, 1,2-dichloroethyl, 1-chloropropyl, 3-chloropropyl, 1-chlorobutyl, 1-chloropentyl, 1-chlorohexyl, 4-chlorobutyl and the like.

When R in formula (I) is $C_6$-$C_{12}$ cycloalkyl-$C_pH_{2p}$-, the cycloalkyl groups contain 6 to 8 ring atoms and may optionally bear one or more, preferably one to four, alkyl substituents. Exemplary such cycloalkyl groups are cyclohexyl, 2,6-dimethylcyclohexyl, 3,3,5,5-tetramethylcyclohexyl, 2-methylcyclohexyl, 2-ethylcyclohexyl, 4-propylcyclohexyl, 5-butylcyclohexyl, 2,3-dimethylcyclohexyl, 2,4-dimethylcyclohexyl, 2,5-dimethylcyclohexyl, 2,3,4-trimethylcyclohexyl, 2,3-dimethyl-5-ethylcyclohexyl, 2,5-dimethyl-6-propylcyclohexyl, 2,4-dimethyl-3-butylcyclohexyl, 2,2,4,4-tetramethylcyclohexyl, 3,3,6,6-tetramethylcyclohexyl, 3,3,4,5,5-pentamethylcyclohexyl, 3,3,4,5,5,6-hexamethylcyclohexyl, 3,3,5-trimethyl-4-ethylcyclohexyl, 3,4,4-trimethyl-5-propylcyclohexyl, cycloheptyl, 3-methylcycloheptyl, 5-propylcycloheptyl, 6-butylcloheptyl, 7-methylcycloheptyl, cyclooctyl, 2-methylcyclooctyl, 3-ethylcyclooctyl, 3,3,4-trimethylcyclooctyl, 3,3,5,5-tetramethylcyclooctyl and the like. Among the presently preferred cycloalkyl—$C_pH_{2p}$— groups represented by R are cyclohexyl, 2,6-dimethylcyclohexyl and 3,3,5,5-tetramethylcyclohexyl. Thus, when R is cycloalkyl—$C_pH_{2p}$—, p is preferably zero or one, most preferably zero. Even more preferred are cycloalkyl—$C_pH_{2p}$— groups containing at least eight carbon atoms in the cycloalkyl portion. Most especially preferred are cycloalkyl—$C_pH_{2p}$— groups wherein the cycloalkyl portion contains 6 to 8 ring atoms and bears at least two alkyl substituents on the ring (e.g. 2,6-dimethylcyclohexyl and 3,3,5,5-tetramethylcyclohexyl).

When a cycloalkyl radical is present in formula (1) as a portion of Ar or as a different portion of R (e.g. when R is —CH₂—X—R₂ wherein R₂ is $C_3$-$C_{12}$ cycloalkyl), then such a cycloalkyl radical can contain 3 to 8 ring atoms and may optionally bear one or more, preferably one to four, alkyl substituents. Examples of such cycloalkyl groups include the examples of $C_6$-$C_{12}$ cycloalkyl radicals recited above as well as the lower homologues, e.g. cyclopropyl, 2-methylcyclopropyl, 3-ethylcyclopropyl, 2-butylcyclopropyl, 3-pentylcyclopropyl, 2-hexylcyclopropyl, cyclobutyl, 2-methylcyclobutyl, 2,3-dimethylcyclobutyl, 3-butylcyclobutyl, 4-hexylcyclobutyl, 2,3,3-trimethylcyclobutyl, 3,3,4,4-tetramethylcyclobutyl, cyclopentyl, 2-methylcyclopentyl, 3-ethylcyclopentyl, 4-butylcyclopentyl, 5-methylcyclopentyl, 3-pentylcyclopentyl, 4-hexylcyclopentyl, 2,3-dimethylcyclopentyl, 2,2,5,5-tetramethylcyclopentyl, 2,3,4-trimethylcyclopentyl, 2,4-dimethyl-3-ethylcyclopentyl, 2,2,3,4,4-pentamethylcyclopentyl, 2,3-dimethyl-3-propylcyclopentyl and the like. When a cycloalkenyl radical is present in formula (I) as a portion of R, corresponding unsaturated radicals such as cyclopentenyl and cyclohexenyl and the like, including alkyl-substituted cycloalkenyl radicals, are contemplated (depending, of course, on the carbon atom limitations in the generic definitions). Again, when R is $C_6$-$C_{12}$ cycloalkenyl—$C_pH_{2p}$—, p is preferably zero or one, most preferably zero. An exemplary $C_6$-$C_{12}$ cycloalkenyl—$C_pH_{2p}$— grouping is 3,5,5-trimethyl-2-cyclohexen-1-yl.

The polycycloalkyl—$C_pH_{2p}$— radicals represented by R are bridged or fused saturated alicyclic hydrocarbon systems consisting of two or more rings, optionally bearing one or more alkyl substituents and having a total of 6 to 18 carbon atoms in the ring portion. The corresponding bridged or fused unsaturated alicyclic hydrocarbon systems are intended by the term "$C_6$-$C_{18}$ polycycloalkenyl—$C_pH_{2p}$—". Such polycycloalkyl and polycycloalkenyl radicals constitute especially preferred embodiments of this invention, most especially the bridged entities. These polycyclic groups represented by R are exemplified by adamantyl (especially 1- or 2- adamantyl), adamantylmethyl (especially 1-adamantylmethyl), adamantylethyl (especially 1-adamantylethyl), bornyl, norbornyl (e.g. exo-norbornyl or endonorbornyl), norbornenyl (e.g. 5-norbornen-2-yl), norbornylmethyl (e.g. 2-norbornylmethyl), norbornylethyl (e.g. 2-norbornylethyl), decahydronaphthyl (e.g. cis or trans decahydronaphth-2-yl), 6,6-dimethylbicyclo[3.1.1] hept-2-en-2-ethyl, (±)-(3-methylnorborn-2-yl)-methyl, 1,3,3-trimethyl-2-norbornyl and 5-norbornene-2-methyl. Thus, in the case of polycyclic radicals, p is preferably 0, 1 or 2.

When R in formula (I) is

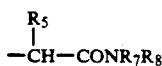

wherein —$NR_7R_8$ represents the residue of a saturated monocyclic secondary amine, such monocycles preferably have 5 to 7 ring atoms optionally containing another hetero atom (—O—, —S— or —N—) in addition to the indicated nitrogen atom, an optionally bear one or more substituents such as phenyl, benzyl and methyl. Illustrative of residues of saturated monocyclic secondary amines which are encompassed by the —$NR_7R_8$ term are morpholino, 1-pyrrolidinyl, 4-benzyl-1-piperazinyl, perhydro-1,2,4-oxathiazin-4-yl, 1- or 4- piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino and 4-phenyl-1-piperazinyl.

The compounds of formula (I) can be prepared by reacting a starting material of the formula

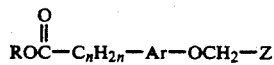 (II)

wherein, R, n and Ar are defined as above and Z is

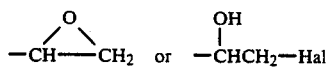

wherein Hal is a halogen atom, especially Cl or Br, with a primary amine of the formula $NH_2R_1$ (III)

wherein $R_1$ is defined as above. This process is preferably carried out in the presence of an inert solvent, although it can be carried out in the absence of solvent. While time and temperature are not critical factors, the reaction is generally conducted at a temperature from about room temperature to about 200° C. (preferably from about 60° to 120° C.), for a period of time from about 30 minutes to 24 hours. Suitable inert solvents include ethers such as dioxane, tetrahydrofuran and ethylene glycol monomethyl ether; aromatic hydrocarbons such as benzene, toluene or xylene; lower alcohols such as methanol, ethanol and isopropanol; and esters such as ethyl acetate, dimethylformamide and dimethylsulfoxide. The process is frequently carried out in the presence of a basic compound, for example, an inorganic base such as sodium carbonate, sodium hydroxide, sodium bicarbonate, sodium amide or sodium hydride; or an organic base such as triethylamine, tripropylamine, pyridine, quinoline, DBN (1,5-diazabiscyclo[4.3.0]non-5-ene), DBU (1,8-diazabicyclo[5.4.0]undec-7-ene) or Dabco (1,4-diazabicyclo[2.2.2.]octane or triethylenediamine). The ratio of the amounts of reactants used can be selected over a wide range. It is, however, generally desirable for the amine of formula (III) to be used in an equimolar quantity or in an excess amount, preferably from an equimolar quantity to about seven times the molar quantity.

The starting materials of formula (II) can be conveniently prepared by reacting the corresponding compounds of the formula

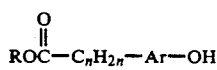 (IV)

wherein R, n and Ar are defined as before, with an epihalogenohydrin of the formula

 (V)

wherein Hal is a halogen atom, especially Cl or Br. This process can be carried out in the presence of a suitable basic compound, for example an inorganic base such a sodium hydroxide, potassium hydroxide, sodium carbonate, potassium carbonate, sodium methoxide, sodium ethoxide, sodium hydride, sodium metal, potassium metal or sodium amide, or an organic basic compound such as piperidine, pyridine, triethylamine, DBN, DBU or Dabco, in the presence or absence of a solvent. Suitable solvents are, for example, a lower alcohol such as methanol, ethanol or isopropanol; a ketone such as acetone; an ether such as dioxane, tetrahydrofuran or ethylene glycol monomethyl ether; or an aromatic hydrocarbon such as benzene, toluene or xylene. In this reaction, the epihalogenohydrin of formula (V) ordinarily can be used in an equimolar to excess quantity, preferably about 5 to 15 times the molar quantity of the formula (IV) starting material. The process can be conducted at a temperature between about 0° and 150° C., preferably at from about 50° to about 100° C. Usually, the reaction product is a mixture of the corresponding (2,3-epoxy)propoxy and 3-halogeno-2-hydroxypropoxy compounds encompassed by formula (II) and can be used as such to prepare the formula (I) compounds.

The starting materials of formula (IV) can be prepared by esterification of carboxylic acids of the formula $$HOOC-C_nH_{2n}-Ar-OH \qquad (VI)$$

wherein n and Ar are defined as before, or the corresponding acid chlorides or acid anhydrides, by reaction with an alcohol of the formula $$ROH \qquad (VIII)$$

wherein R is defined as before. Reaction conditions, solvents and the like vary with the particular reactants employed. Generally speaking, when an acid of formula (VI) is utilized as the starting material, the process is conducted in the presence of a conventional esterification catalyst, e.g. an inorganic acid such as hydrogen chloride gas, concentrated sulfuric acid, phosphoric acid, polyphosphoric acid, boron trifluoride or hypochlorous acid, or an organic acid such as trifluoroacetic acid, trifluoromethanesulfonic acid, napthalensulfonic acid, p-toluenesulfonic acid, benzenesulfonic acid, ethanesulfonic acid, trifluoromethanesulfonic acid anhydride, thionyl chloride, acetone dimethyl acetal and the like. A cation exchange resin may also be used as the catalyst. The reaction can be carried out in the presence or absence of solvent, at a temperature between about −20° to about 200° C., preferably between about 0° and about 150° C., for a period of time from about 10 minutes to about 20 hours. If a solvent is employed, an inert solvent is desirable, for example, an aromatic hydrocarbon such as benzene, toluene or xylene; a hydrogenated hydrocarbon such as chloroform, dichloromethane, dichloroethane or carbon tetrachloride; or an ether such as diethyl ether, tetrahydrofuran, dioxane or ethylene glycol monomethyl ether. The ratio of amount of a compound of formula (VI) to an alcohol of the formula ROH is not subject to any specific restriction and may be suitably selected from a wide range. While usually it is desirable that the latter is used in an excess quantity in the absence of the solvent, in the presence of the solvent it is desirable that the latter is used in an equimolar to 5 times the molar quantity of the former, more preferably an equimolar to 2 times the molar quantity of the former. This reaction can advantageously be effected by using a drying agent such as anhydrous calcium chloride, anhydrous cupric sulfate, anhydrous calcium sulfate, phosphorus pentoxide or the like.

Alternatively, an acid of formula (VI) can be converted to the corresponding salt of the type $$M^+ {}^-OOC-C_nH_{2n}-Ar-OH \qquad (VIII)$$

where n and Ar are defined as before and $M^+$ is $Na^+$ or the like; that salt can then be reacted with a halide of the formula $$R-Hal \qquad (IX)$$

where R is defined as before and Hal is halogen, preferably Cl or Br, to afford the corresponding starting material of formula (IV).

The compounds of the invention which contain a sulfinyl (SO) or sulfonyl (SO$_2$) group can be prepared by oxidation of the corresponding sulfur-containing compounds of the invention. Thus, for example, a compound of formula (I) wherein R is $-CH_2-X-R_2$ wherein X is S can be treated with one equivalent of m-chloroperbenzoic acid to afford the corresponding sulfinyl derivative, while treatment of the thio compound with two equivalents of m-chloroperbenzoic acid yields the corresponding sulfonyl derivative. Thus, the compounds of formula (I) wherein R contains a sulfur atom, e.g. the compounds in which R is $$-CH_2-X-R_2 \quad \text{or} \quad -\overset{R_3}{\underset{|}{CH}}-X-R_4$$

wherein X is S and R$_2$, R$_3$ and R$_4$ are defined above, are of value not only as soft β-adrenergic agents but also as chemical intermediates to the corresponding soft drugs in which X is SO or SO$_2$.

The compounds of the present invention can also be prepared by esterification of the corresponding acid of the formula $$HOOC-C_nH_{2n}-Ar-O CH_2\overset{OH}{\underset{|}{C}H}CH_2NHR_1 \qquad (X)$$

wherein n, Ar and R$_1$ are defined as above, under conditions similar to the esterification of a compound of formula (VI) as described above.

Equivalent to the compounds of formula (I) for the purposes of this invention are the corresponding acid addition salts formed with pharmaceutically acceptable acids. Illustrative of such acids are inorganic acids such as hydrochloric acid, sulfuric acid, hydrobromic acid and the like; and organic acids such as acetic acid, oxalic acid, succinic acid, maleic acid, fumaric acid, malic acid, tartaric acid, citric acid, malonic acid, methanesulfonic acid, benzoic acid and the like.

The compounds prepared by the procedures detailed above can easily be isolated and purified by usual separation means, e.g. solvent extraction, dilution, recrystallization, column chromatography or preparative thin-layer chromatography.

The compounds of the present invention also includes their optical isomers.

For therapeutic use, e.g. in the treatment of angina pectoris and arrhythmias, a compound of formula (I) or its salt can be conveniently administered in the form of a pharmaceutical composition containing the formula (I) compound or its salt and a pharmaceutically acceptable carrier therefor. Suitable carriers vary with the desired form of the pharmaceutical composition and may include diluents or excipients such as fillers, binders, wetting agents, disintegrators, surface-active agents, lubricants and the like.

The compound of the invention or its salt may be formulated together with the carrier into any desired unit dosage form. Typical unit dosage forms include tablets, pills, powders, solutions, suspensions, emulsions, granules, capsules, suppositories; injectable solutions and suspensions are particularly preferred.

In the preparation of tablets, carriers which are widely used in this field can be employed, e.g. excipients such as lactose, sucrose, sodium chloride, glucose solution, urea, starch, calcium carbonate, kaolin, crystalline cellulose and silicic acid; binding agents such as water ethanol, propanol, simple syrup, glucose, starch solution, gelatin solution, carboxymethyl cellulose, shellac, methyl cellulose, calcium phosphate and polyvinylpyrrolidone; disintegrators such as dried starch, sodium alginate, agar-agar powder, laminalia powder, sodium bicarbonate, calcium carbonate, Tweens, sodium lauryl sulfate, stearic acid monoglyceride, starch and lactose; disintegration inhibitors such as sucrose, stearin, coconut butter and hydrogenated oil; absorption accelerators such as quaternary ammonium bases and sodium lauryl sulfate; wetting agents such glycerin and starch; adsorbing agents such as starch, lactose, kaolin, bentonite and colloidal silicic acid; and lubricants such as purified talc, stearic acid salts, boric acid powder, Macrogol and solid polyethylene glycol.

In the preparations of pills, carriers which are known and widely used in this field can also be used, for example, excipients such as glucose, lactose, starch, coconut butter, hydrogenated vegetable oils, kaolin and talc; binders such as powdered gum arabic, powdered tragacanth, gelatin and ethanol; and disintegrators such as laminaria and agar-agar. In the case of tablets, they can be further coated with the usual coating materials to make sugar-coated tablets, gelatin film-coated tablets, tablets coated with enteric coatings, tablets coated with films or double-layered tablets and multi-layer tablets.

In order to form suppositories, carriers which are known and widely used in this field can also be used, for example, polyethylene glycols, coconut butter, higher alcohols, esters of higher alcohols, gelatin and semisynthesized glycerides.

In order to prepare formulations suitable for injection, solutions and suspensions are sterilized and are preferably isotonic to blood. In making injectable preparations, carriers which are commonly used in this field can also be used, for example, water, ethyl alcohol, propylene glycol, ethoxylated isostearyl alcohol, polyoxylated isostearyl alcohol, polyoxyethylene sorbitol and sorbitate esters. In these instances, adequate amounts of sodium chloride, glucose or glycerine can be added to make the preparations isotonic.

Furthermore, the usual dissolving agents, buffers, analgesic agents and preservatives can be added, as well as coloring materials, perfumes, seasoning agents, sweetening agents and other medicines, to the pharmaceutical compositions, if necessary or if desired.

The amount of a compound of formula (I) or its acid addition salt to be present in the pharmaceutical composition, e.g. for use in treatment of angina pectoris and arrhythmias, can suitably be selected from a wide range, but usually 1 to 70% by weight of the total composition is preferable.

As to the route of administration, e.g. for angina pectoris, same will vary with the particular composition used. For example, tablets, pills, solutions, suspensions, emulsions, granules and capsules can be administered orally; and injectable preparations can be administered intravenously, either alone or mixed with injection transfusions such as glucose solutions and amino acid solutions. If necessary, the injectable preparations can be administered separately, by the intramuscular, intracutaneous, subcutaneous or intraperitoneal route.

The dosage of the compounds of the present invention is selected according to the usage, purpose and conditions of symptoms. For example, when these compounds are administered therapeutically to patients suffering from angina pectoris, hypertension, or unexpected arrhythmias during surgical operation, usually 0.5–6.0 mg/kg of the compound of general formula (I) or its acid addition salt may be administered.

The present compounds also may be continuously administered at suitable intervals, including 30 minutes to 60 minutes.

The compounds of the present invention and their salts reduce intraocular pressure when applied topically/locally to the eye, thus are of particular use in the treatment of patients with glaucoma or in the treatment of other patients who require lowering of ocular pressure (such as patients with elevated intraocular pressure who may be at risk of developing glaucoma). The instant compounds and their salts can be conveniently administered for these purposes by formulating the selected $\beta$-blocker, in an effective intraocular pressure lowering amount, together with a non-toxic ophthalmically acceptable carrier therefor. Suitable carriers will be apparent to those skilled in the art of ophthalmic formulations. Obviously, the choice of suitable carriers will depend on the exact nature of the particular dosage form desired, e.g. whether the $\beta$-blocker is to be formulated into an ophthalmic solution or suspension (typically for use as eye drops), an ophthalmic ointment or cream or an ophthalmic gel. Preferred dosage forms are solutions, which contain a major amount of water in addition to the active ingredient. Minor amounts of other ingredients such as pH adjusters (e.g. a base such as NaOH), emulsifiers or dispersing agents, buffering agents, preservatives, wetting agents and jelling agents (e.g. methylcellulose) may also be present. Most preferably, the ophthalmic composition is a sterile, isotonic, buffered aqueous solution. Generally speaking, the ophthalmic composition containing the instant $\beta$-blockers may be prepared and may contain the various inert ingredients or carriers as previously described in the patent or non-patent literature as being suitable for ophthalmic compositions comprising known $\beta$-blockers such as timolol and labetolol. The amount of the $\beta$-blocker of this invention which will be present in the ophthalmic composition will of course vary with the particular $\beta$-blocker employed and the type of formulation selected. Generally speaking the composition will contain 0.01 to 5% of a compound of formula (I), preferably 0.25 to 2.5%; in other words, each mL of solution will contain 0.1 to 50 mg, preferably 2.5 to 25 mg, of the free base. The dose administered ophthalmically will be selected according to the particular compound employed and the size and condition of the patient, but in any event will be a quantity sufficient to cause a significant reduction in intraocular pressure.

In order to further illustrate the present invention and the advantages thereof, specific examples of compounds of formula (I) are given below, it being understood that these examples are intended only as illustrative and are not in any way limitative. Also exemplified below are the preparation of selected starting material sand the preparation of structurally related esters which are not claimed herein (e.g. the lower alkyl esters whose syntheses are given in EXAMPLE 5 below and which are homologues of the ethyl ester specifically described by Barrett et al, U.S. Pat. No. 3,663,607, issued May 16, 1972).

In the examples to follow, all melting points are uncorrected and were obtained by using electrothermal capillary melting point apparatus.

EXAMPLE 1

Cyclohexyl alcohol (6 g), 4-hydroxyphenylacetic acid (7.6 g), p-toluenesulfonic acid (1 g) and benzene (300 mL) were refluxed with continuous water separation for 8 hours. The mixture was cooled and washed with a 10% Na₂CO₃ solution, then with water. Drying over MgSO₄ and evaporation of the solvent in vacuo gave 12.24 g of cyclohexyl 4-hydroxyphenylacetate. That compound can be represented by the formula:

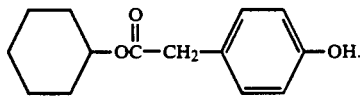

EXAMPLE 2

A mixture of 2,6-dimethylcyclohexyl alcohol (11.4 g), 4-hydroxyphenylacetic acid (9.12 g), p-toluenesulfonic acid (1 g) and benzene (300 mL) was refluxed with continuous water separation for 20 hours. The mixture was filtered and the filtrate was washed with a 10% Na₂CO₃ solution, then with water. Drying over MgSO₄ and evaporation in vacuo afforded 8.02 g of 2,6-dimethylcyclohexyl 4-hydroxyphenylacetate. That product has the structural formula:

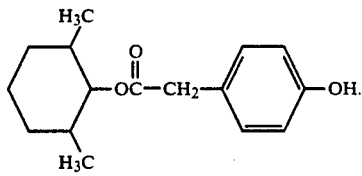

EXAMPLE 3

A mixture of 4-hydroxyphenylacetic acid (6.08 g), 3,3,5,5-tetramethylcyclohexyl alcohol (6.24 g), p-toluenesulfonic acid (1 g) and benzene (300 mL) was refluxed for 8 hours with continuous water separation. The mixture was cooled and washed with 10% Na₂CO₃, then with water. Drying over MgSO₄ and evaporation in vacuo yielded 12.3 g of 3,3,5,5-tetramethylcyclohexyl 4-hydroxyphenylacetate. That product, which can be represented by the structural formula

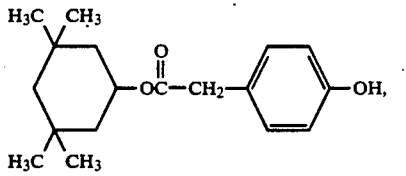

is characterized by the following NMR (CDCl₃, TMS, ppm): 7.00 (d, J=8Hz, 2H), 6.60 (d, J=8Hz, 2H), 5.00 (broad, 1H), 3.40 (s, 2H) and 1.80–0.80 (m, 18H).

EXAMPLE 4

A mixture of ethyl 4-(2-hydroxy-3-isopropylamino)-propoxyphenylacetate (29.5 g), 1N NaOH solution (200 mL), and ethanol (200 mL) was refluxed for 1 hour, and then evaporated in vacuo. The residue was dissolved with water (200 mL). The insoluble material was removed by filtration. To the filtrate was added dilute hydrochloric acid, and the crystals were filtered, washed with water, dried and recrystallized from water to yield 20 g of 4-(2-hydroxy-3-isopropylamino)propoxyphenylacetic acid, as colorless needles melting at 212°–213° C. That compound has the structural formula:

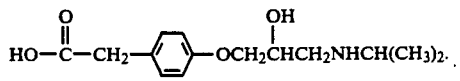

EXAMPLE 5

A mixture of 4-hydroxyphenylacetic acid (9.12 g, 0.06 mol), n-propanol (40 mL) and SOCl₂ (2 mL, 0.028 mol) was refluxed for 3 hours, then evaporated in vacuo. The residue was extracted with ethyl acetate (200 mL, washed with 10% Na₂CO₃, then water dried (MgSO₄), and evaporated in vacuo to give n-propyl 4-hydroxyphenylacetate as an oil. A solution of n-propyl 4-hydroxyphenylacetate (5.8 g, 0.03 mol) in epichlorohydrin (50 mL) was refluxed in the presence of DBU (2 mL, 0.014 mol) for 2 hours. After the excess epichlorohydrin was removed, the residue was refluxed with isopropylamine (20 mL, 0.23 mol) in n-propanol (50 mL), for 4 hours, then was evaporated in vacuo. The residue was crystallized from n-hexane to yield 3.8 g (41%) of n-propyl 4-(2-hydroxy-3-isopropylamino)-propoxyphenylacetate, melting at 61°–62° C. and having the structural formula:

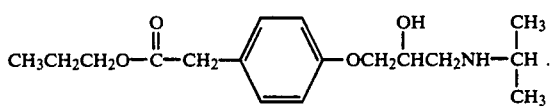

The above method was used with minor modifications for the synthesis of a number of other esters, i.e.:

Isopropyl 4-(2-hydroxy-3-isopropylamino)propoxyphenylacetate, crystallized from petroleum ether, melting at 59°–60° C.;

n-Butyl 4-(2-hydroxy-3-isopropylamino)propoxyphenylacetate, crystallized from a mixture of chloroform and hexane, melting at 48°–49° C.; and Benzyl 4-(2-hydroxy-3-isopropylamino)propoxyphenylacetate, crystallized from a mixture of chloroform and hexane, melting at 73°–74° C.

n-Butyl 4-(2-hydroxy-3-tert-butylamino)propoxyphenylacetate was prepared similarly to the n-butyl ester described above, replacing the isopropylamine starting material in the last step with tert-butylamine. The crude ester was dissolved in dimethyl carbonate and a solution of oxalic acid in dimethyl carbonate was added. The crystals were removed by filtration and recrystallized from acetone to yield 9 g (25%) of n-butyl 4-(2-hydroxy-3-tert-butylamino)propoxyphenylacetate oxalate hydrate, melting at 112°–114° C.

All final products prepared above gave satisfactory elementary analysis ±0.4% C, H, N. NMR and ir spectra were consistent with structure.

EXAMPLE 6

Cyclohexyl 4-hydroxyphenylacetate (9.18 g) in epichlorohydrin (50 mL) was refluxed for 2 hours in the presence of DBU (1 mL). The mixture was evaporated in vacuo, and the residue was refluxed with isopropylamine (20 mL) in acetonitrile (100 mL) for 4 hours, then evaporated in vacuo. A solution of oxalic acid in acetone was added to a solution of the residue in acetone. The crystals were removed by filtration and recrystallized from acetone to yield 6.05 g of cyclohexyl 4-(2-hydroxy-3-isopropylamino)propoxyphenylacetate oxalate 3/4 hydrate, melting at 131°-132° C. Elementary analysis and NMR and ir spectra were consistent with structure. The free base has the formula:

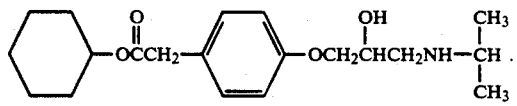

EXAMPLE 7

2,6-Dimethylcyclohexyl 4-hydroxyphenylacetate (8.00 g) was refluxed with epichlorohydrin (50 mL) in the presence of DBU (1 mL) for 2 hours, and evaporated in vacuo. The residue was refluxed with isopropylamine (20 mL) in acetonitrile (100 mL) for 4 hours, then evaporated to dryness in vacuo. To a solution of the residue was added a solution of oxalic acid in acetone, and the crystals were removed by filtration, washed with acetone, an recrystallized from acetone to yield 6.4 g of 2,6-dimethylcyclohexyl 4-(2-hydroxy-3-isopropylamino)propoxyphenylacetate oxalate hydrate, melting at 89°-91° C. Elementary analysis and NMR and ir spectra were consistent with structure. The free base has the structural formula:

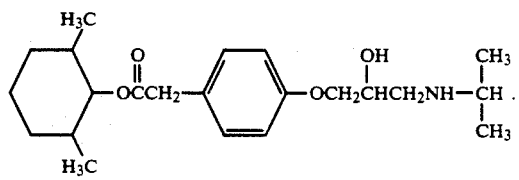

EXAMPLE 8

3,3,5,5-Tetramethylcyclohexyl 4-hydroxyphenylacetate (10.86 g) was dissolved in 8% methanolic KOH solution (20 mL), and evaporated to dryness in vacuo. Epichlorohydrin (500 mL) was added to the residue, and the mixture was refluxed for 2 hours, then evaporated in vacuo. The residue was extracted with benzene (200 mL), washed, dried, evaporated in vacuo, and refluxed with isopropylamine (20 mL) in acetonitrile for 8 hours, then evaporated in vacuo. A solution of oxalic acid in acetone was added to a solution of the residue in acetone. The crystals were removed by filtration and recrystallized from acetone to yield 8.06 g of 3,3,5,5-tetramethylcyclohexyl 4-(2-hydroxy-3-isopropylamino)propoxyphenylacetate oxalate ¾ hydrate, melting at 96°-97° C. Elementary analysis and NMR and ir spectra were consistent with structure. The free base has the structural formula:

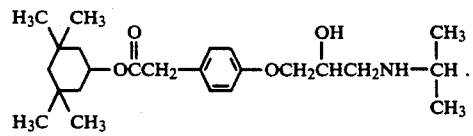

EXAMPLE 9

A solution of 4-(2-hydroxy-3-isopropylamino)propoxyphenyl acetic acid (13.4 g) in cyclohexyl alcohol (50 mL) was saturated with hydrogen chloride gas under cooling, then was heated at 70° C. for 4 hours. Excess cyclohexyl alcohol was evaporated in vacuo. The residue was dissolved in water (200 mL) and adjusted to pH 9 with 10% $Na_2CO_3$ solution. The oily material was extracted with chloroform (200 mL), washed with water, dried, and evaporated in vacuo. The residue was dissolved in acetone (100 mL) and adjusted to pH 5 with 10% oxalic acid in acetone. The crystals were removed by filtration, washed with acetone, dried and recrystallized from acetone to yield 11.8 g of cyclohexyl 4-(2-hydroxy-3-isopropylamino)propoxyphenylacetate oxalate 3/4 hydrate, melting at 131°-132° C.

EXAMPLE 10

Use of the starting materials indicated below in the general esterification procedure described in EXAMPLE 1 affords the indicated products:

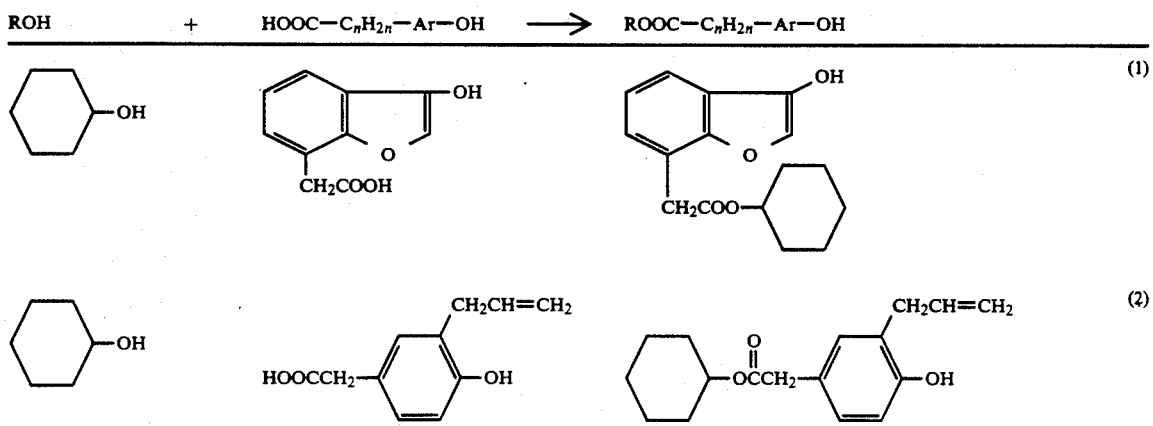

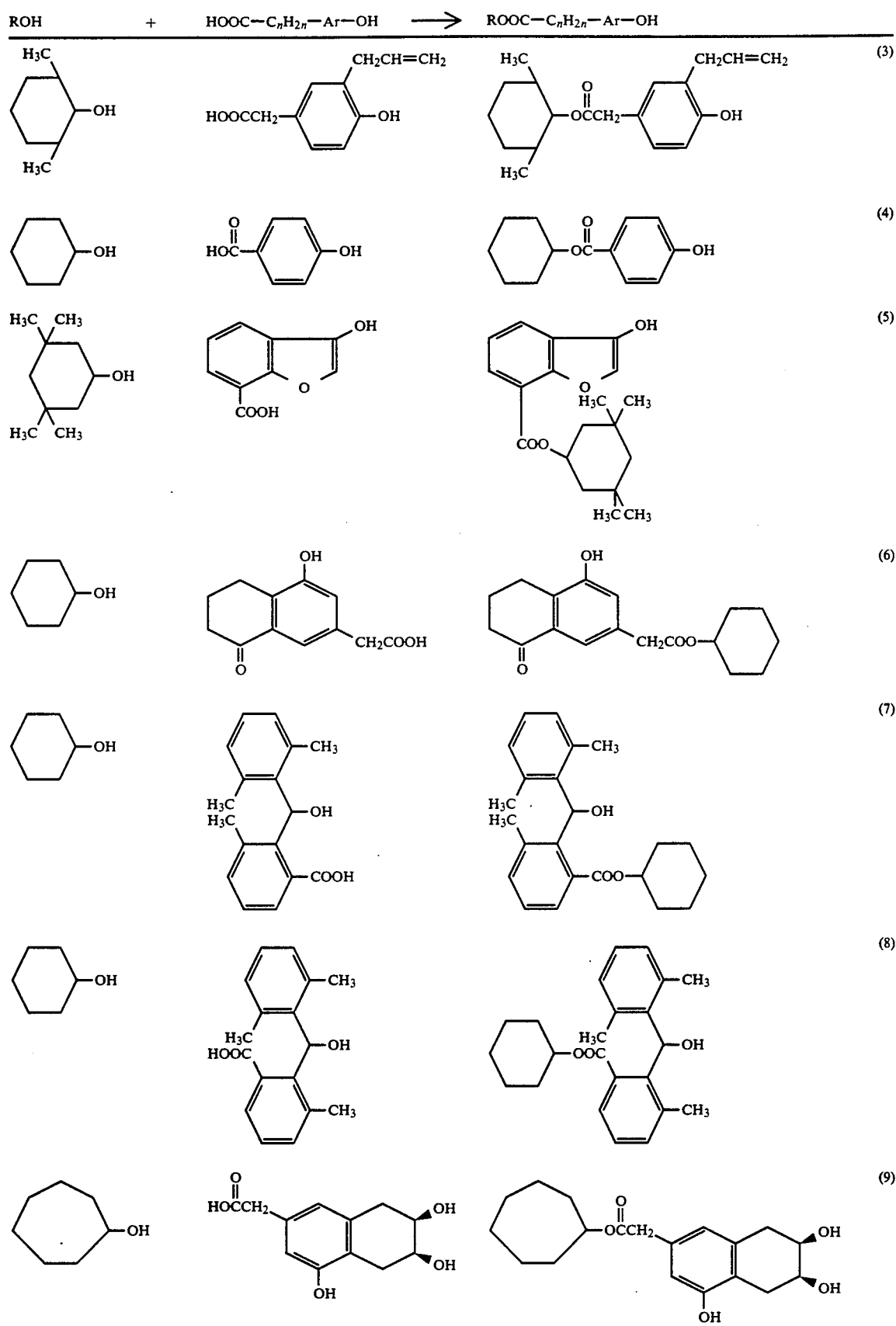

-continued
| ROH | + | HOOC—$C_nH_{2n}$—Ar—OH | → | ROOC—$C_nH_{2n}$—Ar—OH | |
|---|---|---|---|---|---|
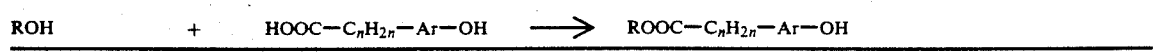
(10)
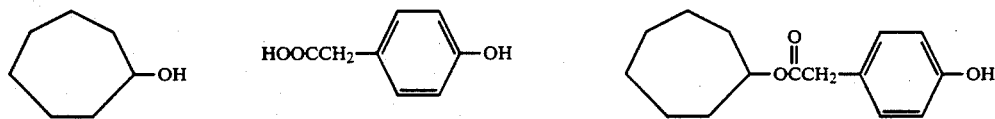
(11)
(12)
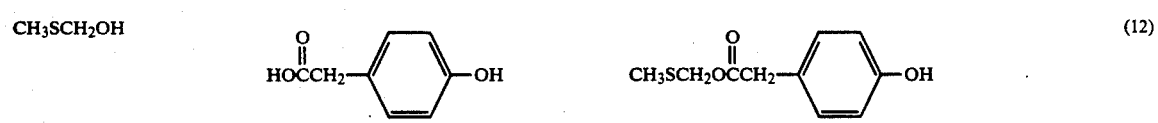
(13)
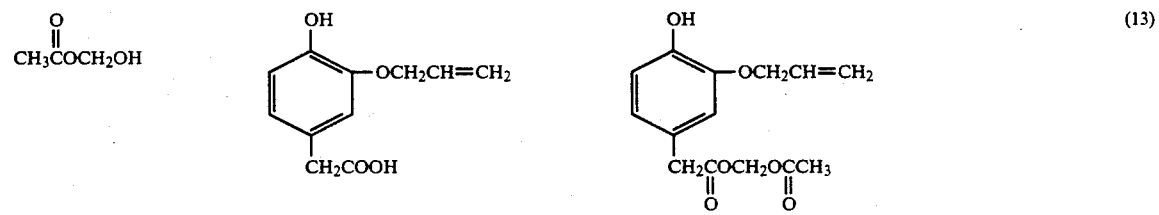
(14)
(15)
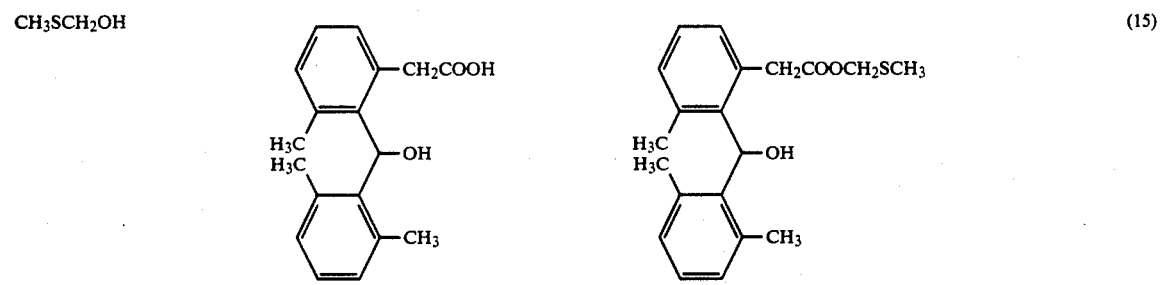
(16)
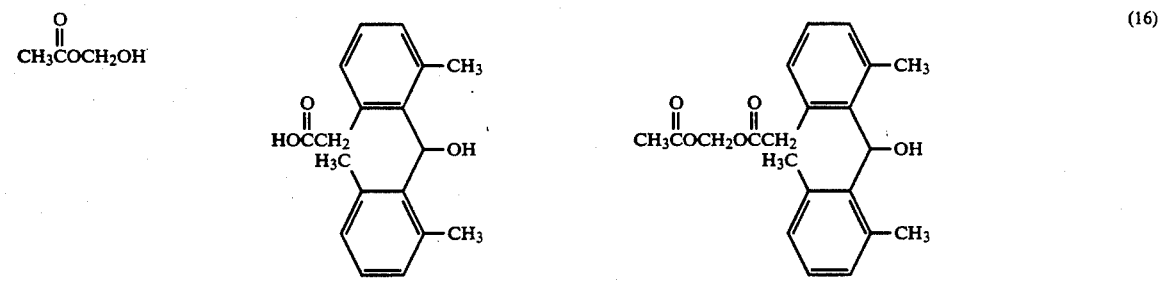
(17)
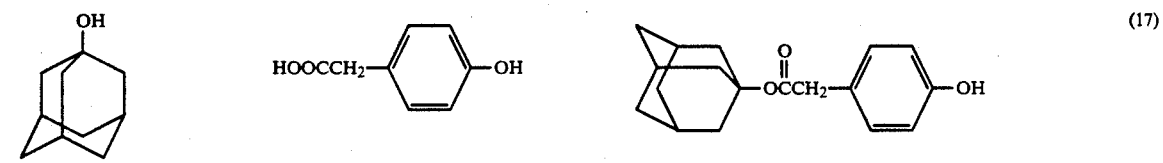

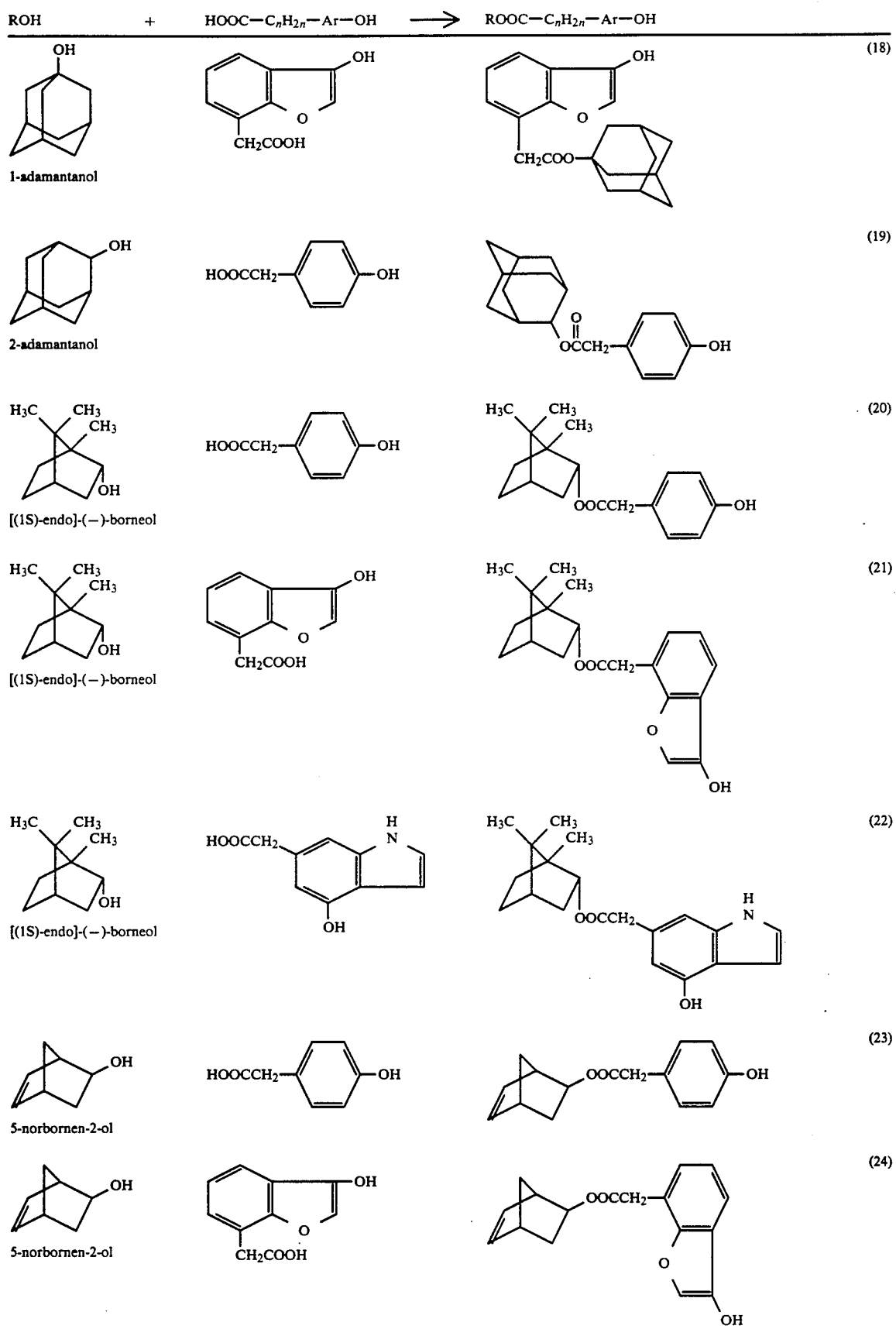

-continued
| ROH | + | HOOC—C$_n$H$_{2n}$—Ar—OH | → | ROOC—C$_n$H$_{2n}$—Ar—OH |
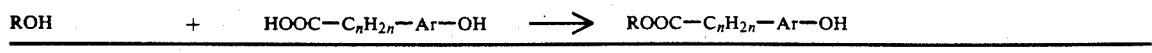
(25)
(26)
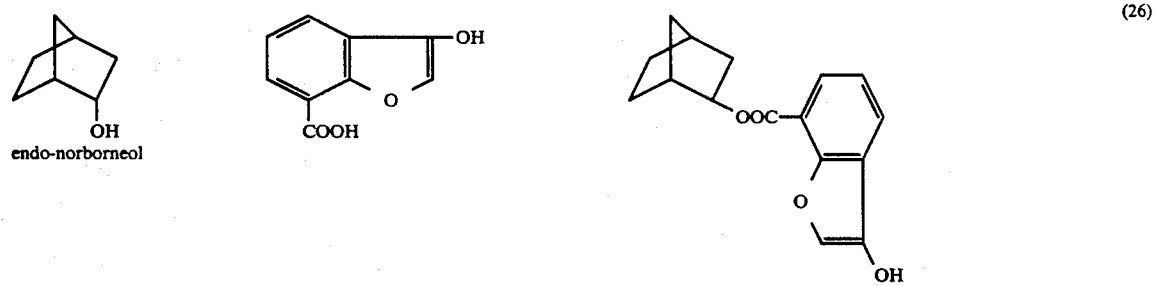
(27)
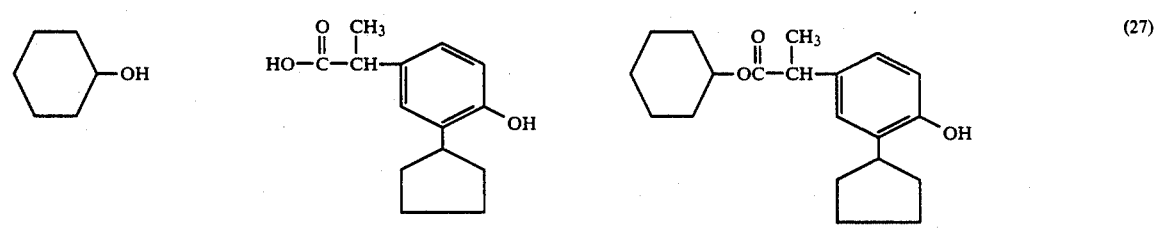
(28)
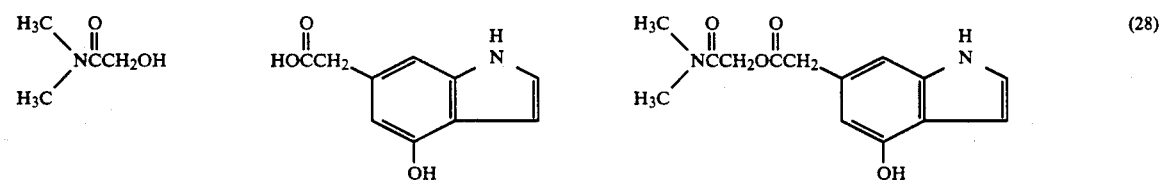
(29)
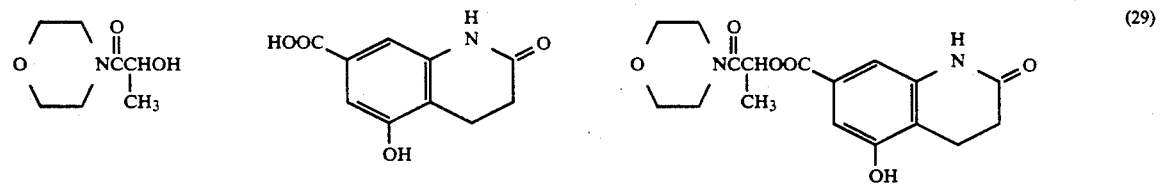
(30)
(31)
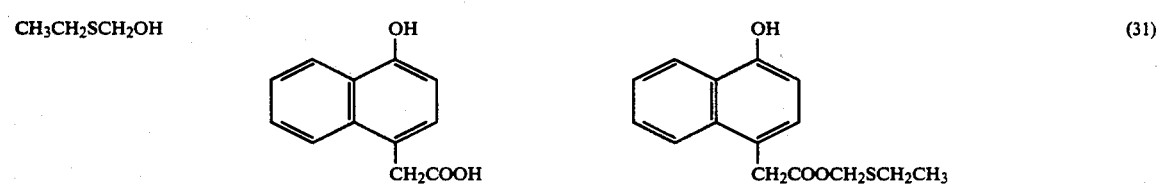
(32)
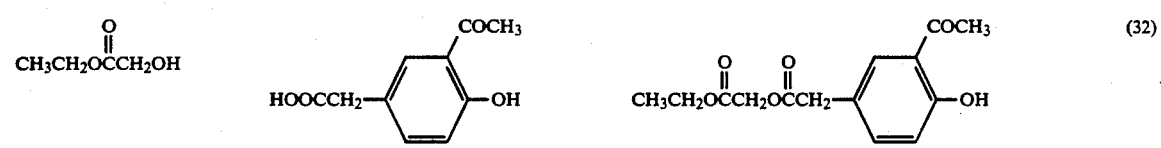
(33)
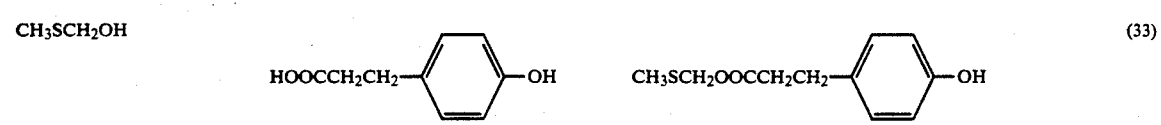

-continued
| ROH | + | HOOC—$C_nH_{2n}$—Ar—OH | → | ROOC—$C_nH_{2n}$—Ar—OH | |
|---|---|---|---|---|---|
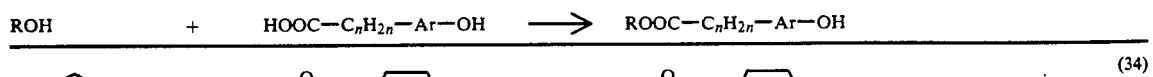
(34)
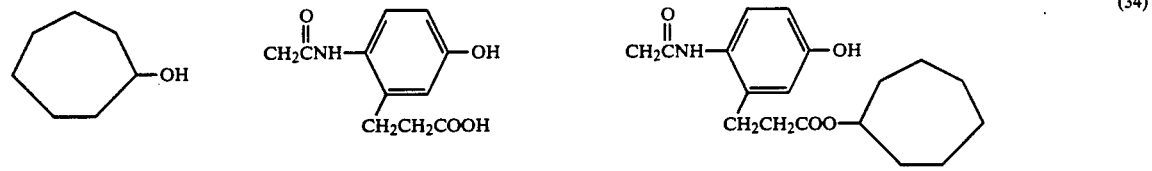
(35)
1-adamantanemethanol
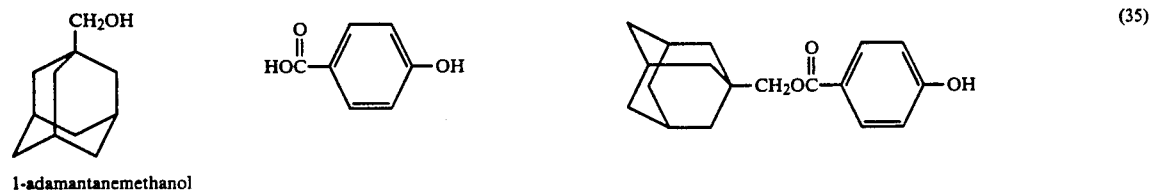
(36)
1-adamantaneethanol
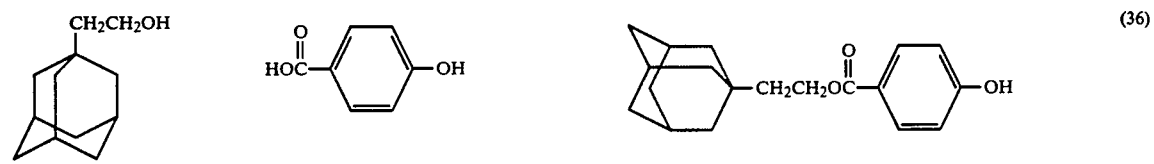
(37)
*2-norbornaneethanol, prepared from 2-norbornaneacetic acid by reduction, e.g. with LiAlH₄
(38)
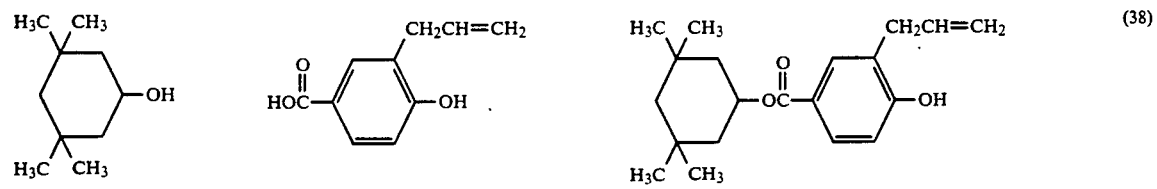
(39)
decahydro-2-naphthol
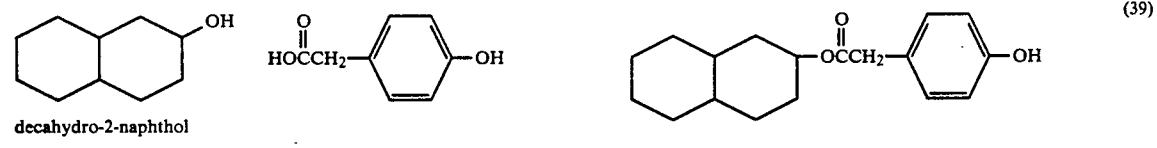
(40)
(1S)-(−)-nopol, or 6,6-dimethylbicyclo [3.1.1]-hept-2-ene-2-ethanol
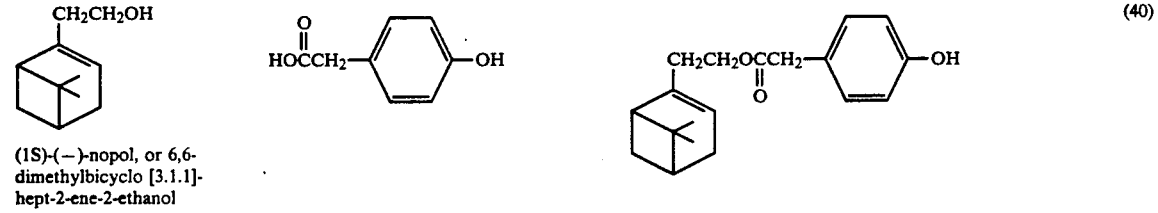
(41)
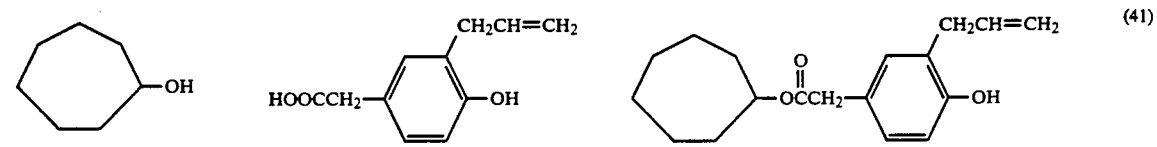

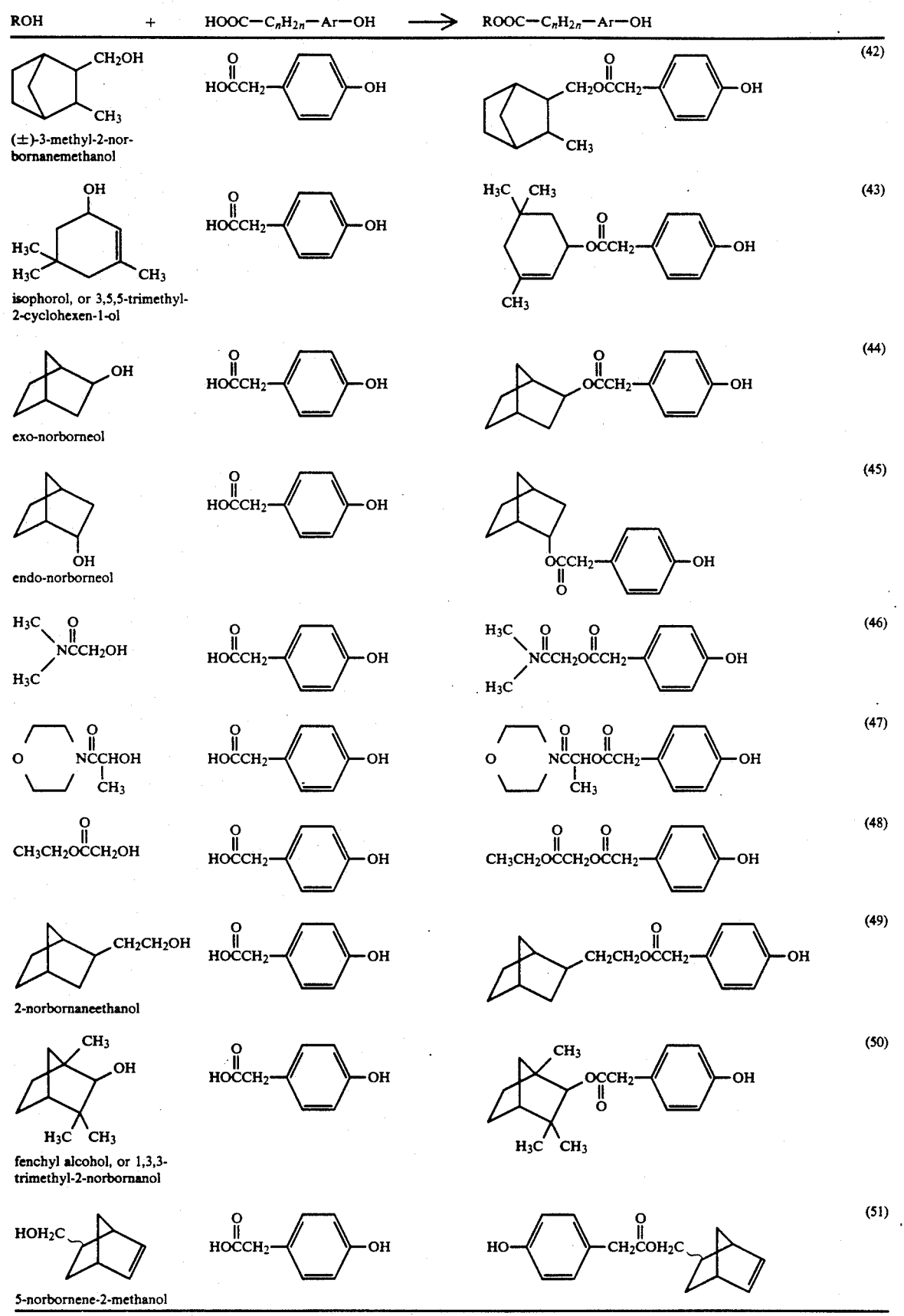

EXAMPLE 11

Substitution of an equivalent quantity of the products of EXAMPLE 10 in the general procedures of EXAMPLE 6 [i.e. reaction of a compound of the formula $ROOC-C_nH_{2n}-Ar-OH$ with an epihalogenohydrin such as epichlorohydrin, followed by reacting the resultant intermediate(s) with the appropriate primary amine] affords, after appropriate isolation, the following compounds of the invention:

| STARTING MATERIAL | $\underset{ROC-C_nH_{2n}-Ar-OCH_2CHCH_2NHR_1}{\overset{O\quad\quad\quad OH}{\|\quad\quad\quad\quad\quad\|}}$ |
|---|---|
| 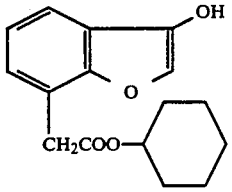<br>(1) | 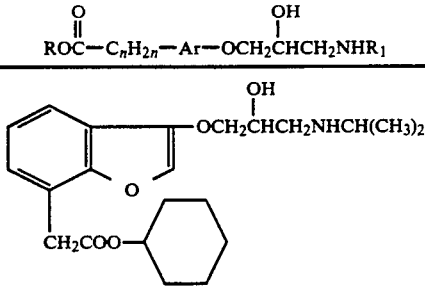<br>(AN ANALOGUE OF BUFUROLOL) |
| 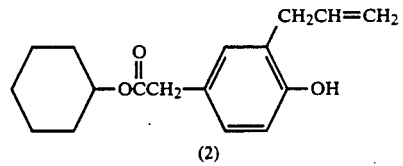<br>(2) | 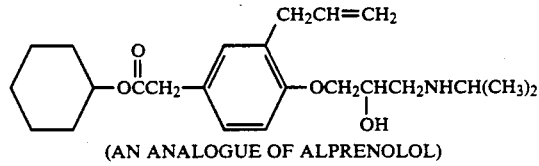<br>(AN ANALOGUE OF ALPRENOLOL) |
| 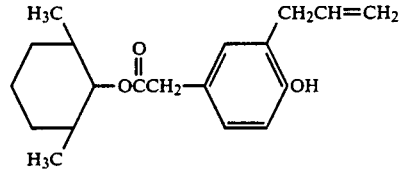<br>(3) | 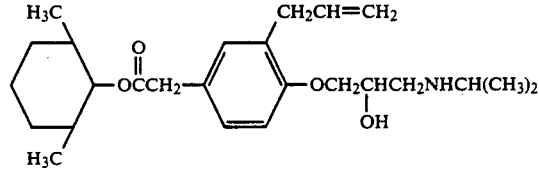<br>(AN ANALOGUE OF ALPRENOLOL) |
| 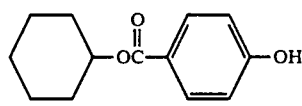<br>(4) | 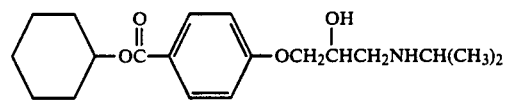<br>(AN ANALOGUE OF METOPROLOL) |
| 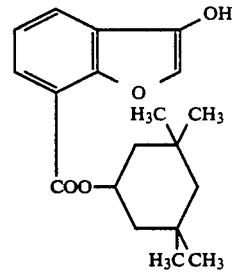<br>(5) | 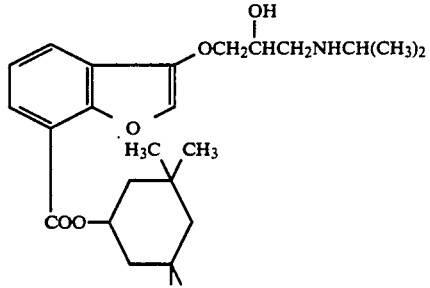<br>(AN ANALOGUE OF BUFUROLOL) |
| 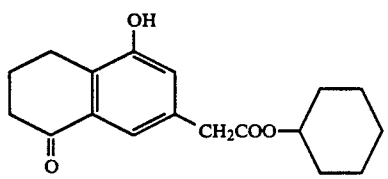<br>(6) | 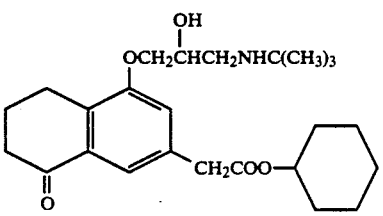<br>(AN ANALOGUE OF BUNOLOL) |

-continued

| STARTING MATERIAL | $\overset{O}{RO\overset{\|}{C}}-C_nH_{2n}-Ar-O\overset{OH}{CH_2\overset{\|}{C}HCH_2NHR_1}$ |
|---|---|
| (7) | (AN ANALOGUE OF XIPRANOLOL) |
| (8) | (AN ANALOGUE OF XIPRANOLOL) |
| (9) | (AN ANALOGUE OF NADOLOL) |
| (10) | (AN ANALOGUE OF METOPROLOL) |
| (11) | (AN ANALOGUE OF TIPRENOLOL) |
| (12) | (AN ANALOGUE OF METOPROLOL) |

-continued

| STARTING MATERIAL | $ROC(=O)-C_nH_{2n}-Ar-OCH_2CH(OH)CH_2NHR_1$ |
|---|---|
| (13) | (AN ANALOGUE OF OXPRENOLOL) |
| $CH_3COCH_2OCCH_2$—[C₆H₄]—OH (diester, para-OH phenyl) | $CH_3COCH_2OCCH_2$—[C₆H₄]—$OCH_2CH(OH)CH_2NHCH(CH_3)_2$ |
| (14) | (AN ANALOGUE OF METOPROLOL) |
| (15) 2,6-dimethylphenyl-CH(OH)- substituted with CH₂COOCH₂SCH₃ and methyl group | (AN ANALOGUE OF XIPRANOLOL) — OCH₂CH(OH)CH₂NHCH(CH₃)₂ |
| (16) $CH_3COCH_2OCCH_2$— with dimethylaryl-CH(OH)- | (AN ANALOGUE OF XIPRANOLOL) |
| (17) adamantyl-OC(=O)CH₂—[C₆H₄]—OH | adamantyl-OC(=O)CH₂—[C₆H₄]—$OCH_2CH(OH)CH_2NHCH(CH_3)_2$ (AN ANALOGUE OF METOPROLOL) |
| (18) benzofuran-OH with CH₂COO-adamantyl | benzofuran-$OCH_2CH(OH)CH_2NHCH(CH_3)_2$ with CH₂COO-adamantyl (AN ANALOGUE OF BUFUROLOL) |
| (19) adamantyl-OCCH₂—[C₆H₄]—OH | adamantyl-OCCH₂—[C₆H₄]—$OCH_2CH(OH)CH_2NHCH(CH_3)_2$ (AN ANALOGUE OF METOPROLOL) |
| (20) bornyl-OOCCH₂—[C₆H₄]—OH | bornyl-OCCH₂—[C₆H₄]—$OCH_2CH(OH)CH_2NHCH(CH_3)_2$ (AN ANALOGUE OF METOPROLOL) |

5,135,926

-continued

| STARTING MATERIAL | $\underset{ROC}{\overset{O}{\|}}-C_nH_{2n}-Ar-OCH_2\overset{OH}{\underset{\|}{C}}HCH_2NHR_1$ |
|---|---|
| (21) | (AN ANALOGUE OF BUFUROLOL) |
| (22) | (AN ANALOGUE OF PINDOLOL) |
| (23) | (AN ANALOGUE OF METOPROLOL) |
| (24) | (AN ANALOGUE OF BUFUROLOL) |
| (25) | (AN ANALOGUE OF METOPROLOL) |
| (26) | (AN ANALOGUE OF BUFUROLOL) |

-continued
| STARTING MATERIAL | $ROC(O)-C_nH_{2n}-Ar-OCH_2CH(OH)CH_2NHR_1$ |
|---|---|
| 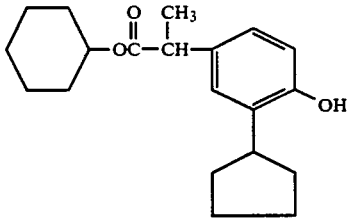<br>(27) | 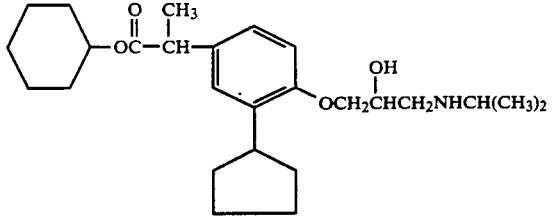<br>(AN ANALOGUE OF PENBUTOLOL) |
| 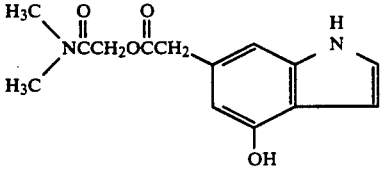<br>(28) | 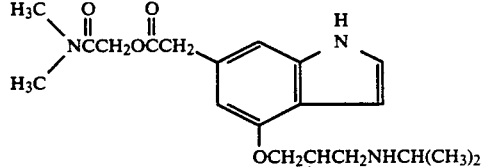<br>(AN ANALOGUE OF PINDOLOL) |
| 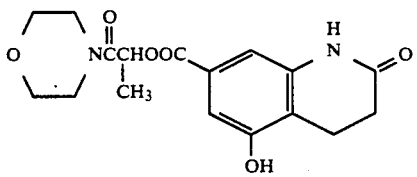<br>(29) | 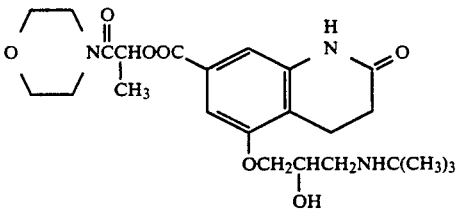<br>(AN ANALOGUE OF CARTEOLOL) |
| 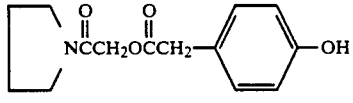<br>(30) | 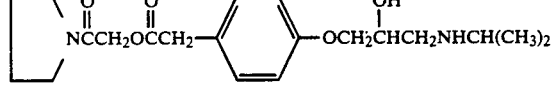<br>(AN ANALOGUE OF METOPROLOL) |
| 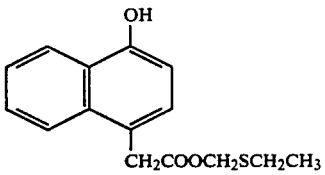<br>(31) | 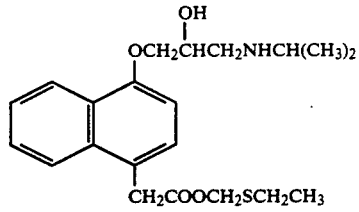<br>(AN ANALOGUE OF PROPRANOLOL) |
| 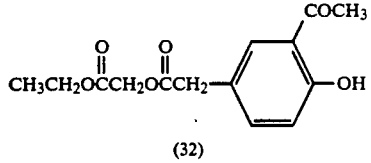<br>(32) | 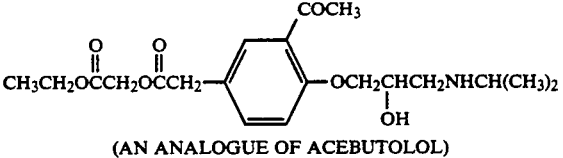<br>(AN ANALOGUE OF ACEBUTOLOL) |
| 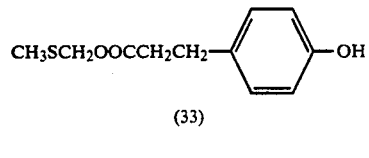<br>(33) | 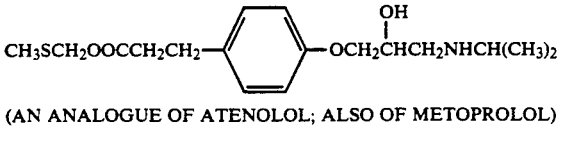<br>(AN ANALOGUE OF ATENOLOL; ALSO OF METOPROLOL) |

| STARTING MATERIAL | $ROOC-C_nH_{2n}-Ar-OCH_2CHCH_2NHR_1$ with OH on middle carbon |
|---|---|
| (34) | (AN ANALOGUE OF PRACTOLOL) |
| (35) | (AN ANALOGUE OF METOPROLOL) |
| (36) | (AN ANALOGUE OF METOPROLOL) |
| (37) | (AN ANALOGUE OF METOPROLOL) |
| (38) | (AN ANALOGUE OF ALPRENOLOL) |
| (39) | (AN ANALOGUE OF METOPROLOL) |
| (40) | (AN ANALOGUE OF METOPROLOL) |
| (41) | (AN ANALOGUE OF ALPRENOLOL) |
| (42) | (AN ANALOGUE OF METOPROLOL) |

-continued

| STARTING MATERIAL | $ROC(O)-C_nH_{2n}-Ar-OCH_2CH(OH)CH_2NHR_1$ |
|---|---|
| (43) [3,3-dimethyl-5-methyl-cyclohex-4-enyl ester of 4-hydroxyphenylacetic acid] | (AN ANALOGUE OF METOPROLOL) — corresponding $-OCH_2CH(OH)CH_2NHCH(CH_3)_2$ |
| (44) [norbornan-2-yl ester of 4-hydroxyphenylacetic acid] | (AN ANALOGUE OF METOPROLOL) |
| (45) [norbornan-2-yl ester of 4-hydroxyphenylacetic acid, alt. orientation] | (AN ANALOGUE OF METOPROLOL) |
| (46) $(CH_3)_2NC(O)CH_2OC(O)CH_2-C_6H_4-OH$ | (AN ANALOGUE OF METOPROLOL) |
| (47) morpholino-$NC(O)CH(CH_3)OC(O)CH_2-C_6H_4-OH$ | (AN ANALOGUE OF METOPROLOL) |
| (48) $CH_3CH_2OC(O)CH_2OC(O)CH_2-C_6H_4-OH$ | (AN ANALOGUE OF METOPROLOL) |
| (49) [norbornyl-$CH_2CH_2OC(O)CH_2-C_6H_4-OH$] | (AN ANALOGUE OF METOPROLOL) |
| (50) [bornyl ester of 4-hydroxyphenylacetic acid] | (AN ANALOGUE OF METOPROLOL) |
| (51) $HO-C_6H_4-CH_2C(O)OCH_2$-norbornenyl | $(H_3C)_2CHNHCH_2CH(OH)CH_2O-C_6H_4-CH_2C(O)OCH_2$-norbornenyl (AN ANALOGUE OF METOPROLOL) |

EXAMPLE 12

Treatment of the sulfur-containing compounds of the invention listed below with one equivalent of m-chloroperbenzoic acid affords the corresponding sulfinyl derivatives of the invention, while treatment of the thio compounds with two equivalents of m-chloroperbenzoic acid yields the corresponding sulfonyl derivatives of the invention.

| THIO COMPOUND | SULFINYL COMPOUND | SULFONYL COMPOUND |
|---|---|---|
| CH₃SCH₂OCCH₂—⟨C₆H₄⟩—OCH₂CHCH₂NHCH(CH₃)₂ (with O= and OH) | CH₃SOCH₂OCCH₂—⟨C₆H₄⟩—OCH₂CHCH₂NHCH(CH₃)₂ (with O= and OH) | CH₃SO₂CH₂OCCH₂—⟨C₆H₄⟩—OCH₂CHCH₂NHCH(CH₃)₂ (with O= and OH) |
| (12) | | |
| 2,6-dimethylphenyl-CH(OCH₂CHCH₂NHCH(CH₃)₂)(OH)-2,6-dimethylphenyl with CH₂COOCH₂SCH₃ | 2,6-dimethylphenyl-CH(OCH₂CHCH₂NHCH(CH₃)₂)(OH)-2,6-dimethylphenyl with CH₂COOCH₂SOCH₃ | 2,6-dimethylphenyl-CH(OCH₂CHCH₂NHCH(CH₃)₂)(OH)-2,6-dimethylphenyl with CH₂COOCH₂SO₂CH₃ |
| (15) | | |
| naphthyl(OCH₂CHCH₂NHCH(CH₃)₂, OH)(CH₂COOCH₂SCH₂CH₃) | naphthyl(OCH₂CHCH₂NHCH(CH₃)₂, OH)(CH₂COOCH₂SOCH₂CH₃) | naphthyl(OCH₂CHCH₂NHCH(CH₃)₂, OH)(CH₂COOCH₂SO₂CH₂CH₃) |
| (31) | | |
| CH₃SCH₂OOCCH₂—⟨C₆H₄⟩—OCH₂CHCH₂NHCH(CH₃)₂ (with OH) | CH₃SOCH₂OOCCH₂—⟨C₆H₄⟩—OCH₂CHCH₂NHCH(CH₃)₂ (with OH) | CH₃SO₂CH₂OOCCH₂—⟨C₆H₄⟩—OCH₂CHCH₂NHCH(CH₃)₂ (with OH) |
| (33) | | |

EXAMPLE 13

A mixture of 4-hydroxyphenylacetic acid (9.12 g, 0.06 mol), methanol (50 mL) and SOCl$_2$ (2 mL, 0.028 mol) was refluxed for 3 hours. The residue was cooled, diluted with ethyl acetate (20 mL), washed first with aqueous 5% Na$_2$CO$_3$ solution and then twice with water (100 mL), then dried over anhydrous MgSO$_4$, filtered and evaporated in vacuo to give methyl 4-hydroxyphenylacetate as an oil.

A solution of methyl 4-hydroxyphenylacetate (8.72 g) in epichlorohydrin (50 mL) was refluxed in the presence of DBU (2 mL, 0.014 mol) for 2 hours. Excess epichlorohydrin was removed under vacuum. The oily product was refluxed with isopropylamine (20 mL, 0.23 mol) in acetonitrile (100 mL) for 4 hours, then was evaporated in vacuo. The free amine base which separated was taken up in acetone (25 mL) and a molar equivalent amount of oxalic acid was added dropwise. The acetone solution was concentrated and the residue was partitioned between ether (100 mL) and 1M aqueous KOH solution (100 mL). The ether layer was separated, 1N HCl (30 mL) was added, the acidic layer was separated, and ethyl ether (100 mL) and 1M aqueous KOH solution (30 mL) were added to it. The resultant ether layer was separated, dried over anhydrous MgSO$_4$, filtered and evaporated in vacuo. The oily residue (5.43 g, 0.01 mol) was dissolved in 25 mL of acetone, and oxalic acid (2.5 g, 0.01 mol) in acetone was added dropwise with stirring and cooling. The product which separated was filtered, dried and crystallized from a mixture of ethyl acetate and acetone. The resultant oxalate salt of methyl 4-(2-hydroxy-3-isopropylamino)-propoxyphenylacetate, obtained in 82% yield, melted at 58°–59° C. NMR and elemental analysis confirmed the identity of the product.

EXAMPLE 14

A mixture of 4-hydroxyphenylacetic acid (9.12 g, 0.06 mol), absolute ethanol (50 mL) and SOCl$_2$ (2 mL, 0.028 mol) was refluxed for 3 hours. The residue was cooled, diluted with ethyl acetate (200 mL), washed first with dilute aqueous sodium bicarbonate (100 mL) and then twice with water (100 mL), then was dried over anhydrous MgSO$_4$, filtered and evaporated in vacuo. Ethyl 4-hydroxyphenylacetate was obtained as an oil.

A solution of ethyl 4-hydroxyphenylacetate (9.20 g) in acetone (50 mL) and epichlorohydrin (50 mL) was refluxed in the presence of DBU (2 mL, 0.014 mol) for 2 hours. Excess epichlorohydrin was removed under reduced pressure. The resultant oil was taken up in acetonitrile (100 mL), isopropylamine (20 mL, 0.23 mol) was added and the reaction mixture was refluxed for 4 hours. Evaporation in vacuo afforded an oil. The oil was taken up in acetone (50 mL) and an equivalent amount of oxalic acid in acetone (25 mL) was added gradually. A white crystalline by-product melting at 202°–204° C. separated on cooling. The acetone mother liquor was evaporated and the residue was partitioned between ethyl ether (100 mL) and 1M aqueous KOH solution (100 mL). The ether layer was separated and washed with 1M HCl (50 mL). The acid layer was partitioned between anhydrous ethyl ether (100 mL) and 1M aqueous KOH solution (100 mL). The ether layer was separated, dried over anhydrous MgSO$_4$, filtered and evaporated to dryness. The residue (5.30 g) was dissolved in acetone (25 mL). An equivalent amount of oxalic acid (2.52 g, 0.1 mol) was dissolved in acetone (25 mL) and was added dropwise, with constant stirring. The reaction mixture was allowed to cool, and the product which separated was filtered and crystallized from a mixture of acetone and ethyl acetate. The resultant oxalate salt of ethyl 4-(2-hydroxy-3-isopropylamino)propoxyphenyl)acetate melted at 82°–84° C. NMR and elemental analysis confirmed the identity of the product.

EXAMPLE 15

A mixture of 4-hydroxyphenylacetic acid (7.6 g, 0.05 mol), cyclohexyl alcohol (6 g, 0.06 mol), p-toluenesulfonic acid (1 g, 0.006 mol) and benzene (300 mL) was refluxed with continuous water separation for 8 hours. The mixture was cooled and washed, first with aqueous 5% Na$_2$CO$_3$ solution, then twice with water, then was dried over anhydrous MgSO$_4$. Evaporation of the solvent in vacuo gave cyclohexyl 4-hydroxyphenylacetate.

A solution of cyclohexyl 4-hydroxyphenylacetate in epichlorohydrin (30 mL) was refluxed for 2 hours in the presence of DBU (1 mL, 0.007 mol). Excess epichlorohydrin was removed in vacuo. The residue was refluxed with isopropylamine (20 mL, 0.23 mol) in acetonitrile (100 mL) for 4 additional hours, then the mixture was allowed to stand at room temperature for 24 hours and evaporated in vacuo. The residue was partitioned between ethyl ether (100 mL) and aqueous 1M KOH solution (100 mL). The ether layer was separated and 1N HCl (30 mL) was added to it. The acid layer was separated and washed with ethyl ether (100 mL). The resultant ether layer was separated, washed with aqueous 1M KOH solution (30 mL) and water and then dried over anhydrous MgSO$_4$, filtered and evaporated in vacuo. The residue was dissolved in acetone (50 mL) and an equivalent amount of oxalic acid in acetone (25 mL) was added dropwise, with stirring. The oxalate salt of cyclohexyl 4-(2-hydroxy-3-isopropylamino)-propoxyphenylacetate which was isolated in 50.2% yield melted at 130°–132° C. The free base has the structure depicted in EXAMPLE 6.

EXAMPLE 16

3,3,5,5-Tetramethylcyclohexanol (7.81 g, 0.05 mol), 4-hydroxyphenylacetic acid (7.6 g, 0.05 mol), p-toluenesulfonic acid (2 g) and benzene (200 mL) were refluxed with continuous water separation for 8 hours. The reaction mixture was evaporated, the oily residue was dissolved in ethyl acetate (100 mL), washed first with aqueous 5% NaHCO$_3$ solution (100 mL) and then twice with water (200 mL), then dried over anhydrous MgSO$_4$. The solvent was evaporated under reduced pressure to give 3,3,5,5-tetramethylcyclohexyl 4-hydroxyphenylacetate as a solid (7.00 g, 82.0% yield).

3,3,5,5-Tetramethylcyclohexyl 4-hydroxyphenylacetate was taken up in acetone (25 mL), combined with epichlorohydrin (20 mL) with stirring and refluxed for 2 hours in the presence of DBU (1 mL, 0.007 mol). The reaction mixture was evaporated. The oily residue was taken up in acetonitrile (50 mL). Isopropylamine (20 mL, 0.23 mol) was added and the reaction mixture was refluxed for 4 hours, then was evaporated to give the crude free amine base as an oil. The oil was taken up in acetone and an equivalent amount of oxalic acid (5.2 g, 0.05 mol) was added. The acetone solution was concentrated and partitioned between ether (100 mL) and aqueous 1M KOH solution (50 mL). The ether layer was separated and washed with 1M HCl (50 mL). The acidic layer was basified with aqueous 1M KOH solution and extracted with fresh anhydrous ethyl ether. The ether layer was separated, dried over anhydrous MgSO4, filtered and evaporated. The residue was dissolved in acetone (25 mL), an equivalent amount of oxalic acid in acetone was added, and the oxalate salt of 3,3,5,5-tetramethylcyclohexyl 4-(2-hydroxy-3-isopropylamino)-propoxyphenylacetate which separated on cooling was isolated. The product melted at 96°-98° C. The free base has the structure shown in EXAMPLE 8.

EXAMPLE 17

To a solution of 4-hydroxyphenylacetic acid (7.6 g, 0.05 mol) in ethanol (100 mL) was added potassium hydroxide (2.8 g, 0.05 mol), with stirring and ice cooling. The white crystalline potassium salt which was separated by filtration melted at about 275°-277° C. and was obtained in 90.5% yield.

The potassium salt of 4-hydroxyphenylacetic acid (9.5 g, 0.05 mL) was suspended in dimethylformamide (25 mL). Chloromethyl pivalate (7.53 g, 0.05 mol) was added and the reaction mixture was stirred at room temperature for 24 hours. The reaction mixture was poured into ice water and extracted with ethyl acetate (100 mL). The ethyl acetate layer was washed, first with aqueous 5% NaHCO3 (100 mL) and then twice with water, then was dried over anhydrous MgSO4, filtered and evaporated to yield pivalyloxymethyl 4-hydroxyphenylacetate, melting at 159°-161° C. (yield 70.2%).

EXAMPLE 18

Pivalyloxymethyl 4-hydroxyphenylacetate (7.0 g, 0.05 mol) was dissolved in acetone (50 mL) and epichlorohydrin (40 mL) was added. That mixture was refluxed in the presence of DBU (1 mL, 0.007 mol) for 2 hours, then was allowed to stir at room temperature overnight. The reaction mixture was evaporated in vacuo. The epoxide residue was dissolved in acetonitrile (80 mL), isopropylamine (20 mL, 0.23 mol) was added and the reaction mixture was stirred overnight at room temperature, refluxed for 4 hours and evaporated. The free amine base was purified by extraction with acid and base from ether. After evaporation of the ether, the residual oil was partitioned between ethyl ether and 1M aqueous KOH solution, the ether layer was washed with 1M HCl, the acidic layer was basified with 1M aqueous KOH solution, and fresh anhydrous ethyl ether was added. The ether layer was separated, dried over anhydrous MgSO4 and filtered. An equivalent amount of oxalic acid in acetone was added dropwise. The oxalate salt which separated was filtered and dried. It melted at 123°-124° C. The free base, pivalyloxymethyl 4-(2-hydroxy-3-isopropylamino)propoxyphenylacetate, has the structure:

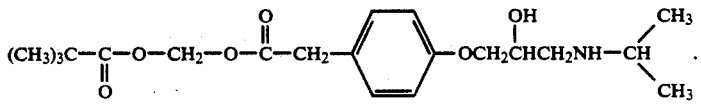

The identity of the product was confirmed by NMR and elemental analysis.

EXAMPLE 19

1-Adamantaneethanol (10 g, 0.05 mol), 4-hydroxyphenylacetic acid (8.43 g, 0.05 mol) and p-toluenesulfonic acid (1 g, 0.006 mol) were refluxed in benzene (100 mL) with continuous water separation for 8 hours, then allowed to stir overnight. The residue was washed, first with 5% aqueous sodium bicarbonate solution (50 mL) and then twice with water (50 mL), then was dried over anhydrous MgSO4 and filtered. The filtrate was concentrated in vacuo. The product, (adamant-1-yl)ethyl 4-hydroxyphenylacetate, was taken up in epichlorohydrin (50 mL) and refluxed for 2 hours in the presence of DBU (1 mL, 0.007 mol). The residue was dissolved in acetonitrile (100 mL) and refluxed with isopropylamine (20 mL, 0.23 mol) for 4 hours. The reaction mixture was evaporated in vacuo and the residue was partitioned between ethyl ether (100 mL) and 0.5N aqueous NaHCO3 solution (100 mL). The ether layer was separated and 1N HCl (30 mL) was added to it. The aqueous layer was separated, 1M aqueous KOH solution (30 mL) was added and the solution was extracted with ether (100 mL). The aqueous layer was discarded and the ether layer was dried over anhydrous MgSO4, filtered and evaporated in vacuo. The oily product was dissolved in acetone (25 mL) and an equivalent quantity of oxalic acid in acetone (25 mL) was added dropwise, with stirring. The acetone was evaporated in vacuo and the residue was partitioned between ether (100 mL) and 1M aqueous KOH solution (100 mL). The ether layer was separated, dried over anhydrous MgSO4, filtered and concentrated in vacuo. The oily residue was dissolved in acetone (25 mL) and an equivalent amount of oxalic acid in acetone (25 mL) was added dropwise, with stirring. The product which separated was removed by filtration, dried and recrystallized from acetone. The oxalate salt of (adamant-1-yl)ethyl 4-(2-hydroxy-3-isopropylamino)propoxyphenylacetate thus obtained melted at 95°-97° C. Yield 70.9%. The free base has the structure:

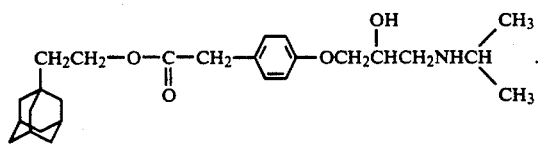

NMR and elemental analysis were consistent with the assigned structure.

EXAMPLE 20

1-Adamantanemethanol (8.31 g, 0.05 mol), 4-hydroxyphenylacetic acid (7.6 g, 0.05 mol) and p-toluenesulfonic acid (1 g, 0.006 mol) were refluxed in benzene (100 mL) with continuous water separation for 8 hours. The reaction mixture was allowed to cool with stirring overnight, then was washed, first with water (100 mL), then with aqueous 5% NaHCO3 solution (100 mL), then twice more with water (100 mL). Drying over anhydrous MgSO4, filtering and concentrating in vacuo afforded (adamant-1-yl)methyl 4-hydroxyphenylacetate, which was then combined with epichlorohydrin (50 mL) and refluxed for 2 hours in the presence of DBU (1 mL, 0.007 mol). Excess epichlorohydrin was removed in vacuo. The oily residue was dissolved in acetonitrile (100 mL) and combined with isopropylamine (20 mL, 0.23 mol). The resultant reaction mixture was refluxed for 4 hours. The oily brown residue was partitioned between ethyl ether (100 mL) and 1M aqueous KOH solution (100 mL). The ether layer was separated and to it was added 1N HCl (30 mL). The resultant acid layer was separated and to it were added ethyl ether (100 mL) and 1M aqueous KOH solution (30 mL). The resultant ether layer was separated, dried over anhydrous MgSO$_4$, filtered and evaporated in vacuo to give the free amine base as a crude product. The crude product (5.16 g, 72.5yield) was dissolved in acetone (25 mL), and oxalic acid (1.8 g) in acetone (25 mL) was added dropwise, with stirring. The mixture was allowed to stir for 24 hours with additional acetone. The acetone solution was evaporated and the oily residue was partitioned between ether (100 mL) and 1M aqueous KOH solution (100 mL). The ether solution was dried over anhydrous MgSO$_4$, filtered and concentrated. The oily residue was dissolved in acetone and an equivalent amount of oxalic acid in acetone was added dropwise. The oxalate salt of (adamant-1-yl)methyl 4-(2-hydroxy-3-isopropylamino)propoxyphenylacetate which separated was removed and dried. It melted at 55°–57° C. NMR and elemental analysis were consistent with structure. The free base has the formula:

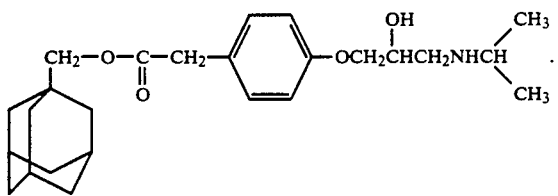

EXAMPLE 21

2-Norboranemethanol (6.34 g, 0.05 mol), 4-hydroxyphenylacetic acid (7.6 g, 0.05 mol), p-toluenesulfonic acid (2 g, 0.006 mol) and benzene (100 mL) were refluxed with continuous water separation for 8 hours. The solvent was evaporated and the residue was dissolved in ethyl acetate (100 mL) and washed, first with 5% aqueous NaHCO$_3$solution (100 mL), then twice with water (200 mL). Drying over anhydrous MgSO$_4$, filtering and evaporation let an oily residue, identified by NMR as the desired (norborn-2-yl)methyl 4-hydroxyphenylacetate. That product was taken up in acetone (50 mL), epichlorohydrin (40 mL) was added, and the reaction mixture was refluxed for 2 hours in the presence of DBU (2 mL, 0.007 mol). The reaction mixture was evaporated in vacuo and the residual oil was taken up in acetonitrile (100 mL). Isopropylamine (20 mL, 0.23 mol) was added and the reaction mixture was refluxed for 4 hours, then evaporated to give the free amine base as an oil. The oil was dissolved in acetone (50 mL) and an equivalent amount of oxalic acid in acetone (25 mL) was added dropwise with stirring. A white crystalline by-product melting at 198°–200° C. separated and was discarded. The acetone was evaporated in vacuo and the oil thus obtained was partitioned between ethyl ether (100 mL) and 1M aqueous KOH solution (100 mL). The ether layer was separated and 1M CHl (50 mL) was added. The acidic layer was separated, neutralized with 1M aqueous KOH solution (50 mL) and extracted with ethyl ether (100 mL). The ether layer was dried over anhydrous MgSO$_4$, filtered and evaporated to give the free amine base as an oil. Water (25 mL) was added to the oil; then oxalic acid (5.4 g, 0.01 mol) in acetone (25 mL) was added dropwise, with constant stirring. The oxalate salt of (norborn-2-yl)methyl 4-(2-hydroxy-3-isopropylamino)-propoxyphenylacetate which separated after cooling was washed with acetone (200 mL) and crystallized from a mixture of ethyl acetate and acetone. It melted at 68°–70° C. The corresponding free base has the structure:

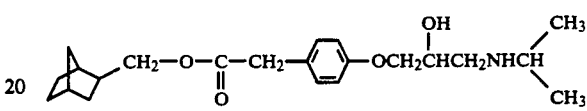

Elemental analysis and NMR were consistent with the assigned structure.

EXAMPLE 25

The potassium salt of 4-hydroxyphenylacetic acid (9.5 g, 0.1 mol) was taken up in a mixture of dimethylsulfoxide (80 mL) and hexamethylphosphoramide (5.37 g, 0.1 mol). 2-Chloroacetamide (13.5 g, 0.3 mol) was added and the reaction mixture was first stirred at room temperature for 24 hours, then heated for 1 hour. The reaction mixture was evaporated, then cooled. The product which separated was taken up in ethyl acetate (150 mL), stirred, filtered and evaporated. The oily residue was partitioned between ethyl acetate (100 mL) and water (100 mL). The organic layer was separated, dried over anhydrous MgSO$_4$, filtered and evaporated to give the desired ester, carbamoylmethyl 4-hydroxyphenylacetate, melting at 85°–87° C., in 48.8% yield.

Carbamoylmethyl 4-hydroxyphenylacetate (10.4 g, 0.01 mol) was taken up in acetone. Epichlorohydrin (40 mL) was added and the reaction mixture was refluxed for 2 hours in the presence of DBU (2 mL, 0.014 mol). The mixture was then evaporated to give an oil, which was dissolved in acetonitrile (100 mL) and then refluxed with isopropylamine (20 mL, 0.23 mol) for 4 hours. The resultant mixture was evaporated in vacuo to give the desired free amine base as an oil. That oil was dissolved in acetone and an equivalent amount of oxalic acid in acetone was added. The acetone solution was concentrated and then partitioned between ethyl ether (100 mL) and 1M aqueous KOH solution (50 mL). The ether layer was separated and extracted with 1M HCl (50 mL). The resultant acidic solution was neutralized with 1M aqueous KOH solution and extracted with ethyl ether. The ether layer was separated, dried over anhydrous MgSO$_4$, filtered and evaporated. The residue was dissolved in acetone and an equivalent amount of oxalic acid in acetone was added. The oxalate salt of carbamoylmethyl 4-(2-hydroxy-3-isopropylamino)propoxyphenylacetate which separated after cooling was removed by filtration and dried. It melted at 93°–95° C. The corresponding free base has the structural formula:

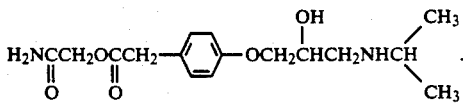

NMR and elemental analysis were consistent with the assigned structure.

In the examples which follow, reference numbers have been assigned to the test compounds as indicated immediately below:

| Compound No. | Name |
|---|---|
| 5 | 4-(2-Hydroxy-3-isopropylamino)propoxyphenylacetic acid |
| 10 | Ethyl 4-(2-hydroxy-3-isopropylamino)propoxyphenylacetate |
| 11 | n-Propyl 4-(2-hydroxy-3-isopropylamino)propoxyphenylacetate |
| 12 | Isopropyl 4-(2-hydroxy-3-isopropylamino)propoxyphenylacetate |
| 13 | n-Butyl 4-(2-hydroxy-3-isopropylamino)propoxyphenylacetate |
| 14 | Benzyl 4-(2-hydroxy-3-isopropylamino)propoxyphenylacetate |
| 15 | Cyclohexyl 4-(2-hydroxy-3-isopropylamino)propoxyphenylacetate oxalate ¼ hydrate |
| 16 | 2,6-Dimethylcyclohexyl 4-(2-hydroxy-3-isopropylamino)propoxyphenylacetate oxalate hydrate |
| 17 | 3,3,5,5-Tetramethylcyclohexyl 4-(2-hydroxy-3-isopropylamino)propoxyphenylacetate oxalate ¼ hydrate |
| 18 | n-Butyl 4-(2-hydroxy-3-tert-butylamino)propoxyphenylacetate oxalate hydrate |

EXAMPLE 23

Kinetic Studies

Analytical Methods. A high pressure liquid chromatography (HPLC) method was developed for the determination of the rate constants. The chromatographic analysis was performed in a system consisting of Waters Associates Model 600-A Solvent Delivery System, Model U-6K Injector and Model 440 Dual Channel Absorbance Detector operated at 254 and 280 nm. A 30 cm × 3.9 mm (internal diameter) reverse phase μBondpack C18 column (Waters Associates), operated at ambient temperature, was used for all separations. When plasma samples were analyzed, the column was protected with a 2.3 cm × 3.9 mm (internal diameter) Guard Column (Waters) packed with μBondpack C18/Corasil packing material. The mobile phase used for the separation of 17 and its degradation product, 5, consisted of water, 1-hexane sulfonic acid in acetic acid (B-6 reagent, Waters), 0.1M triethanolamine and methanol (100:1:100:799). At a flow rate of 2.0 mL/minute, 17 had a retention time of 3.95 minutes and 5 of 1.34 minutes. For the separation of compounds 10–16 and 18 and their degradation product 5, a mobile phase consisting of water, 1-hexane sulfonic acid in acetic acid (B-6 reagent, Waters), 0.1M triethanolamine and methanol (390:1:10:599) was used. At a flow rate of 2.0 mL/minute, 12 had a retention time of 3.79 minutes, 14 of 4.80 minutes, 10 of 2.77 minutes, 11 of 3.85 minutes, 13 of 5.30 minutes, 5 of 1.48 minutes and 18 of 8.39 minutes.

All solvents and reagents used were of UV or analytical reagent grade and were used as obtained. Water was passed through an ion exchange bed and then distilled.

Determination of the Hydrolytic Rate Constants in Aqueous Solutions. A 0.01M phosphate buffer and 0.01N sodium hydroxide solution were prepared from freshly distilled deionized water. This ionic strength was maintained at 0.1M with sodium chloride. The pH of the phosphate buffer was determined at 37.0° C. with a pH meter standardized at this temperature. For determination of the hydrolytic rate constants, a fresh concentrated solution of the ester in methanol was added to the hydrolytic medium previously equilibrated to the desired temperature and mixed thoroughly to result in an initial concentration of about $5 \times 10^{-4}$ mol. liter$^{-1}$. All reactions were run under pseudo first order conditions. Samples of 25 μL were injected into the column at various time intervals and the pseudo first order rate constants were determined from disappearance of the compound by linear regression of natural logarithm of the peak height versus time plots. The half-life and standard error of the rate constant were calculated for each run. The results in 0.01N aqueous sodium hydroxide solution at pH 12.0 and 27.3° C. are listed in TABLE I below.

TABLE I

The Observed Pseudo First Order Hydrolytic Rate Constants (k), Half-Lives (t½) and the Initial Concentrations ($C_0$) in 0.01N Sodium Hydroxide at pH 12.0, Ionic Strength 0.10M (NaCl) and 27.3 ± 0.2° C.

| Compound | k (min$^{-1}$) | t½ (min.) | $C_0$ (mol. liter$^{-1}$) |
|---|---|---|---|
| 10 | 0.117 ± 0.001[a] | 5.91 | 4.5 × 10$^{-4}$ |
| 11 | 0.103 ± 0.001 | 6.73 | 4.6 × 10$^{-4}$ |
| 12 | 2.07 ± 0.03 × 10$^{-2}$ | 33.5 | 9.8 × 10$^{-4}$ |
| 13 | 9.27 ± 0.07 × 10$^{-2}$ | 7.48 | 5.0 × 10$^{-4}$ |
| 14 | 0.208 ± 0.004[a] | 3.33 | 2.2 × 10$^{-4}$ |
| 15 | 4.96 ± 0.03 × 10$^{-2}$ | 14.0 | 1.7 × 10$^{-4}$ |
| 16 | 9.71 ± 0.27 × 10$^{-4}$ | 7.14 | 8.3 × 10$^{-5}$ |
|  | 1.09 ± 0.06 × 10$^{-2}$ | 63.3 | 2.8 × 10$^{-5}$ |
| 17 | 1.56 ± 0.04 × 10$^{-2}$ | 44.4 | 3.0 × 10$^{-5}$ |
| 18 | 7.19 ± 0.04 × 10$^{-2}$ | 9.64 | 8.1 × 10$^{-4}$ |

[a]Average of three runs ± SEM. The rest of data are the average of four runs ± SEM.

In 0.01M phosphate buffer at pH 7.4 and 37° C., the compounds are hydrolyzed very slowly. The half-life of 14 under these conditions was 13 days and that of 11 was 8.7 days.

Determination of the Enzymatic Hydrolytic Cleavage Rates in Human Plasma. The freshly collected plasma used was obtained from the Civitan Regional Blood Center, In. (Gainesville, Fla.) and contained about 80% plasma diluted with anticoagulant citrate phosphate dextrose solution, U.S.P. The plasma was stored in a refrigerator and used within one week from the data it was collected. During the experiment the hydrolytic activity of the plasma was tested by determining its effect on the hydrolytic cleavage rates of 17 and was found to be constant.

A portion of 50 μL of a freshly prepared solution of the compound in methanol was added to 10 mL plasma, previously equilibrated at 37.0° C. in a water bath, and mixed thoroughly to result in an initial concentration of $1 \times 10^{-3}$ mol. liter$^{-1}$. One mL samples of plasma were withdrawn from the test medium, mixed immediately with 4.0 mL ice cold 95% v/v ethanol, centrifuged and the supernatant analyzed by HPLC. The first order hydrolytic rate constant was determined as before in the aqueous solutions and the results are listed in TABLE II below.

TABLE II

The Observed First Order Hydrolytic Rate Constants (k), Half-Lives ($t_{\frac{1}{2}}$) and the Initial Concentrations ($C_0$ in Human Plasma at $37.0 \pm 0.1°$ C. The Hydrolytic Rate Constants Were Obtained by Following the Disappearance of the Compounds by HPLC as a Function of Time.

| Compound | k (min$^{-1}$) | $t_{\frac{1}{2}}$ (min) | $C_0$ (mol. liter$^{-1}$) |
|---|---|---|---|
| 10 | $0.238 \pm 0.010^a$ | 2.91 | $1.6 \times 10^{-3}$ |
| 11 | $0.143 \pm 0.005$ | 4.86 | $2.5 \times 10^{-3}$ |
| 12 | $0.414 \pm 0.001 \times 10^{-2}$ | $1.67 \times 10^2$ | $1.1 \times 10^{-3}$ |
| 13 | $0.612 \pm 0.016$ | 1.13 | $1.4 \times 10^{-3}$ |
| 14 | $0.236 \pm 0.007^a$ | 2.93 | $1.4 \times 10^{-3}$ |
| 15 | $1.46 \pm 0.15^b$ | 0.47 | $5.8 \times 10^{-4}$ |
|  | —$^c$ | — | $5.9 \times 10^{-4}$ |
| 16 | $1.64 \pm 0.14 \times 10^{-2}$ | 42.2 | $2.0 \times 10^{-4}$ |
| 17 | $0.566 \pm 0.027$ | 1.22 | $9.3 \times 10^{-4}$ |
| 18 | $0.351 \pm 0.019$ | 1.98 | $1.5 \times 10^{-3}$ |

$^a$Average of three runs ± SEM.
$^b$Average of four runs ± SEM.
$^c$Essentially no change in the peak height over a period of three hours.

From the hydrolytic stabilities of esters 10–17 in aqueous solution at pH 12, it can be seen that the rate of hydroxide ion catalyzed hydrolysis is generally controlled by the relative steric hindrance at the ester portion. Compound 16 was obtained as a 1:2 mixture of two isomers, separable by HPLC, and in agreement with this, 16 showed biphasic kinetics. While the starting alcohol was a mixture of isomers (potentially six), the ester 16 contained only two of them (cis-, most likely di-equatorial and trans-, axial- equatorial dimethyl cyclohexanol derivatives). The latter one possibly was a d, l mixture, inseparable by simple chromatography. It is assumed that the bulky ester group between the two methyl functions is in equatorial position. The kinetic data are shown in TABLE I.

The relative hydrolysis rates in human plasma (TABLE II) show, however, some unexpected trends: The isopropyl ester 12 is hydrolyzed up to 100 times more slowly then many of the other esters. The isomer of 16, which is more stable in basic conditions, did not hydrolyze in the plasma within 3 hours. As expected, the presence of the t-butyl group on the amine did not affect the hydrolysis rates (13 vs. 18). It is evident, however, that except for the isopropyl derivative 12, the rest of the esters hydrolyzed very fast in the plasma.

EXAMPLE 24

Pharmacological Tests

Initial Drug Screening Protocol. Thirty-two male Sprague-Dawley rats (Blue Spruce Farms) initially weighing 300–450 gm were divided into seven different groups, each for a different drug to be tested: 12(n=4), 14(n=4), 17(n=5), 13(n=4) and 18 (n=3), corresponding to the designated compounds 12, 14, 17, 13 and 18 (number of animals), respectively. The other two groups were controls (n=8, isoproterenol alone pretreated with carrier) and those treated with a known β-blocker, dl-propranolol (n=3). Each animal was anesthetized with sodium pentobarbital (45 mg/kg) and the carotid artery was cannulated with PE-50 tubing. The cannula was subcutaneously threaded around the neck and exteriorized dorsally between the shoulder blades. The cannula was filled with a heparin solution (300 μg/mL) and sealed with a solid 22 gauge stylet. The animals were housed in individual stainless steel cages, and two days were allowed for recovery from the surgery. Food and water were provided ad libitum. On the day of the experiment, the blood pressure and heart rate of each rat were monitored with a pressure transducer (Narco-Bio model P-1000) and the data recorded on a four-channel physiograph (Narco-Bio systems Marck IV). One hour was allowed as an equilibration period before any drugs were administered. All beta blockers were administered intraperitoneally at a dose of 6 mg/kg. Compounds 12 and 14 and dl-propranolol were dissolved in normal saline while compounds 13, 17 and 18 were dissolved in an ethanol:water solution (3:1). Depending on the trial, controls were administered the appropriate carrier. One hour after administration of the blocker, isoproterenol (Isuprel ®, Wintrop Laboratories) was administered subcutaneously at a dose of 25 μg/kg. Blood pressures and heart rate also were recorded 3, 5, 10, 15, 20, 30, 45 and 60 minutes after isoproterenol administration. Both control and experimental animals were unrestrained and free moving in their home cage throughout the experiment. FIG. 1 shows the results in terms of mean change in heart rate following administration of isoproterenol (25 μg/kg s.c.) for compounds 12(O), 14(△), 17(■), 13(□), 18(◇), d,l-propanolol (●) and the control vehicle (▲). A one-way analysis of variance (f29, 6) revealed no significant differences in resting heart rates prior to administration of isoproterenol: 345±19; 405±22; 372±19; 340±14; 307±7; 320±23 and 333±17 beat/minute, respectively. However, significant differences in the mean heart rate response among the 7 groups were observed: *p<0.005; **p<0.025. Comparisons between groups were made by the Newman-Keuls procedure with significance set at the 95% confidence interval. During the first 20 minutes, the group administered compound 17 was significantly different from both control- and compound 18-treated groups. The propranolol-treated group was significantly different for the first 30 minutes. Additionally, the group administered compound 17 and the propranolol-treated group were significantly different than the groups treated with compound 12 and 18 at 10 through 45 minutes following administration of isoproterenol. All data are shown as mean ± standard error of the mean.

Figure 3:
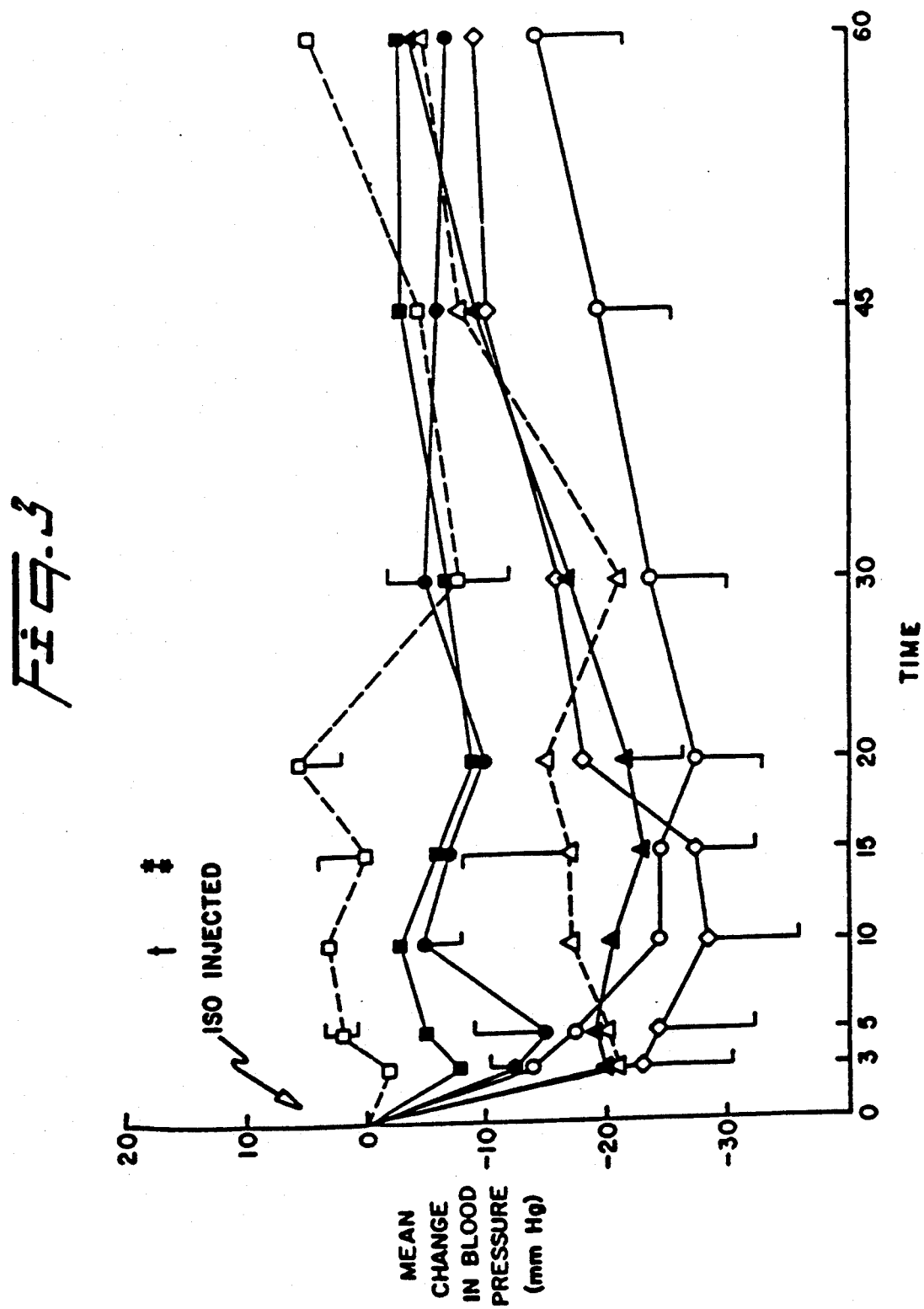
FIG. 3 is a graph plotting the mean change in blood pressure response (mm Hg) with time following subcutaneous administration of 25 μg/kg of isoproterenol to groups or rats pretreated 60 minutes prior to isoproterenol administration with 6 mg/kg of test compound or control vehicle.

FIG. 3 shows the results in terms of mean change in blood pressure following administration of isoproterenol (25 μg/kg s.c.). Symbols are the same as those described for FIG. 1. Statistical analysis revealed that compounds 14 and 13 were significantly lower (p<0.15) than the propranolol and compound 12-treated groups. One-way analysis of variance demonstrated that a significant difference between the seven groups existed at 10 and 15 minutes following administration of isoproterenol: *p<0.01; **p<0.025. At the 10-minute time interval, groups treated with compounds 17 and 13 were significantly different from the group treated with compound 18. The group treated with compound 13 was also different from the compound 12-treated group. At the 15-minute interval, the group pretreated with compound 13 was significantly different from groups pretreated with compound 12, 18 and the control vehicle. Data are shown as mean ± standard error of the mean.

Figure 2:
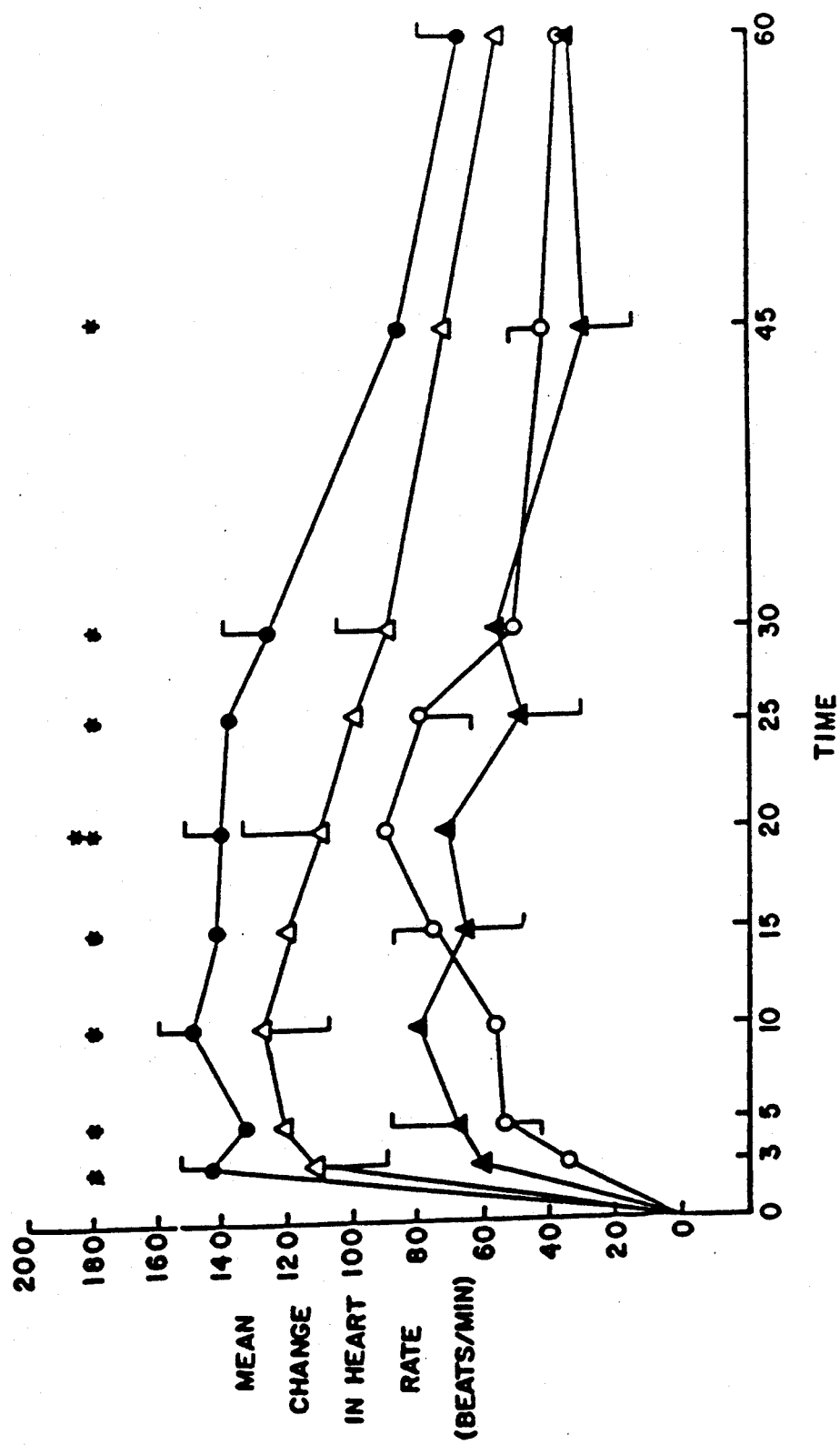
FIG. 2 is a graph plotting the mean change in heart rate response (beats/minute) with time in groups of rats pretreated with control vehicle or with test compound at 15, 60 or 90 minutes prior to administration of isoproterenol (25 μg/kg s.i.) at time zero.

Duration of Action Studies. An additional 38 male Sprague Dawley rats (Blue Spruce Farms) initially weighing 268 to 290 gm were anesthetized with sodium pentobarbital (45 mg/kg i.p.), and the carotid artery was cannulated as previously described. On the data of experimentation, after a one-hour equilibration period, initial baseline conditions of basal heart rate and mean blood pressures were recorded. The beta blocker (17) was administered intraperitoneally at a dose of 6 mg/kg. The drug was dissolved in an ethanol:water solution (3:1). This carrier was administered in the control rats. Isoproterenol (Isurprel ®, Wintrop Laboratories) was then administered (25 μg/kg s.c.), either 15(n=13), 60(n=12) or 90(n=13) minutes after the beta blocker was administered. Blood pressures and heart rates were recorded at 3, 5, 10, 15, 20, 30, 45 and 60 minutes after isoproterenol administration in all three trials. Both control an experimental animals were unrestrained and free moving in their home cages throughout the experiment. Heart rates and mean blood pressure were calculated from the data and a one-way ANOVA was determined at each time interval. The results are shown in FIG. 2 for control vehicle (●) and compound 17 at 15(○), 60(▲) and 90(△) minutes prior to isoproterenol administration at time zero. Resting heart rates were similar in all 4 groups prior to administration of isoproterenol; 342±12; 375±14; 372±19 and 385±17 beats/minute, respectively. One-way analysis of variance (f40, 3) revealed a significant difference in response between the 4 groups during the 45 minutes following administration of isoproterenol: *p<0.005; p<0.025. Comparison between groups demonstrated an attenuated heart rate response when compound 17 was administered either 15 or 60 minutes prior to the administration of isoproterenol. Data are shown as mean ± standard error of the mean.

Cardiovascular Experiments

Method. Healthy, mongrel dogs were anesthetized with a combination of morphine sulfate (2.0 mg/kg, subcutaneously) followed in 20 minutes with pentabarbital sodium (15 mg/kg, intravenously). Supplemental pentabarbital was given as necessary. A femoral vein was catheterized with polyethylene tubing to the level of the heart for injecting drug solutions. A polyethylene tube filled with heparinized saline was inserted through the femoral artery and advanced to the thoracic aorta for the measurement of arterial pressure. The left carotid artery was cannulated with a Millar ® transducer-tip catheter for measurement of left ventricular pressure (LVP). The rising slope of the LVP signal was differentiated to give dP/dt, an estimate of myocardial contractility. Heart rate was determined via a Grass cardiotachometer triggered by the R wave of the lead II EKG. All variables were recorded on a Grass polygraph.

Dose-response curves were constructed for each experimental variable to graded i.v. doses of the β-adrenergic agonist, isoproterenol. A period of 3-5 minutes was allowed after each injection for variables to return to base-line. Following this, one of the four experimental β-adrenergic blocking agents was given i.v. over a one-minute period. Abbreviated dose-response curves (2-3 dose points) were again constructed to isoproterenol at 15, 30, 45, 60, 75 and 90 minutes after the administration of the test blockers. Using a 50-beat per minute (bpm) increase in heart rate as criteria, the degree of blockade was determined by dividing the dose of isoproterenol needed to produce a 50 bpm increase at various times following administration of an antagonist by the dose needed for this effect during the control period. The doses of the experimental β-adrenergic antagonists given were determined from previous experiments to produce an approximate two- or four-fold blockade of the heart rate response to isoproterenol. Results are given in TABLE III and FIG. 4.

TABLE III

Peak Antagonist Activity[a] and Duration of Action[b] of Selected "Soft" β-Adrenergic Blocking Agents

| Compound number | Maximal blockade[a] | | Duration[b] | |
|---|---|---|---|---|
| | Range (min) | Mean (min) | Range (min) | Mean (min) |
| 10 | (15–15) | 15 | 45–60 | −50 |
| 15 | (15–30) | 20 | 75–90 | −85 |
| 16 | (15–60) | 38 | 45–90 | −65 |
| 17 | (30–60) | 40 | 45–90 | −70 |

[a]Time necessary to reach maximal blockade (15 minute measurements). Data were obtained from dose-response curves before and after 1 mg/kg of each agent.
[b]Time after each β-adrenergic blocking agent (1 mg/kg) at which response to isoproterenol had returned to control levels.

Figure 4:
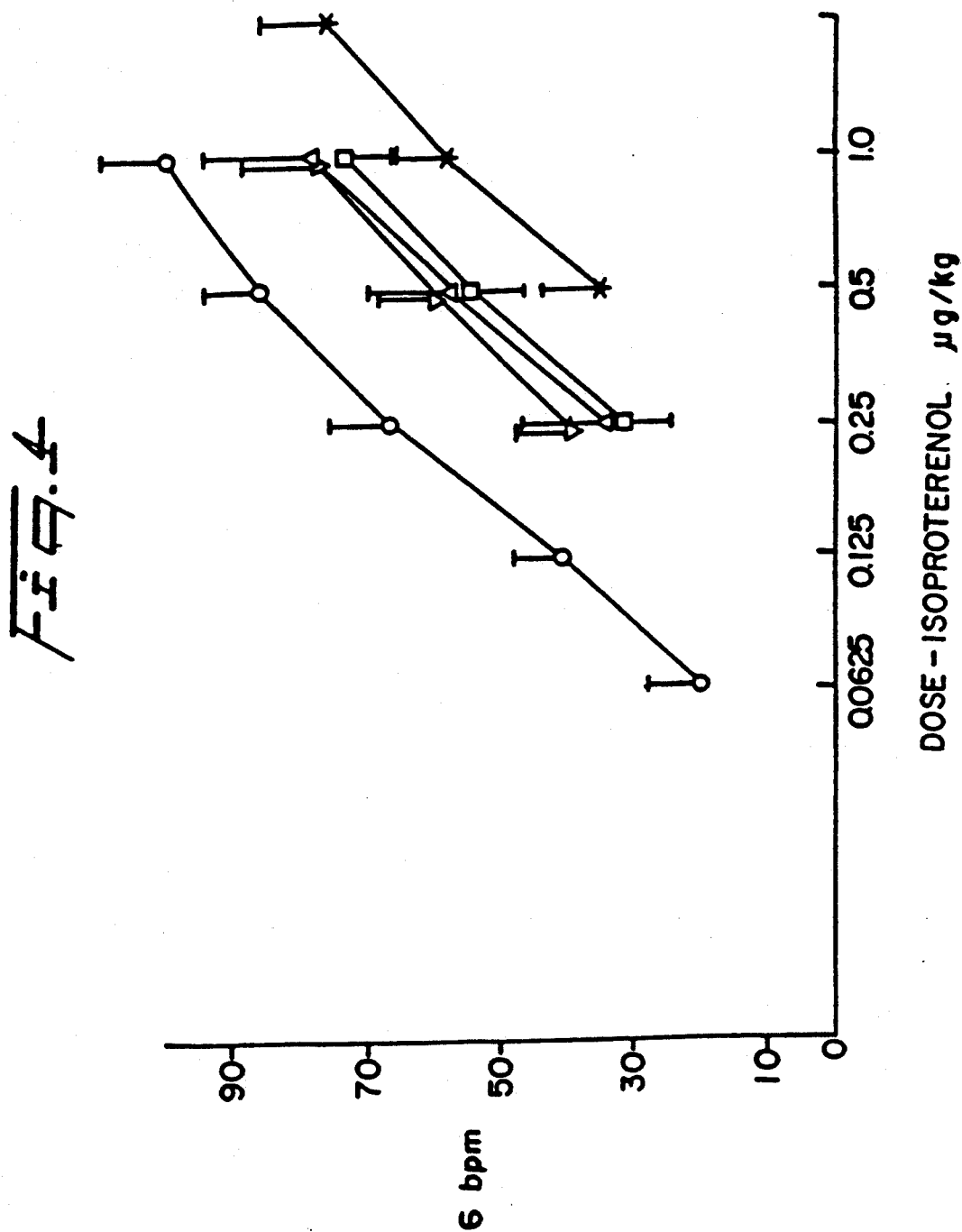
FIG. 4 is a graph plotting the β-adrenergic blocking activities of selected test compounds on the heart rate of dogs.

In FIG. 4, the increase in heart rate (Δbpm) is shown for dogs administered 1 mg/kg of compound 17(∇—∇), 10(△—△), 16(□—□), 15(*—*) and control (—). Baseline values were all around 117±6 bpm. Error bars represent S.E. of mean.

Discussion of Pharmacological Tests

Since, due to high esterase activity in the liver and other organs, esters generally hydrolyze faster in the whole body than in vitro in plasma, and since acid 5 is inactive, not much β-antagonist activity would be expected, unless there is not much correlation between the plasma concentration of the active species and the actual activity (affinity and binding to the receptors). Five compounds, 12, 13, 14, 17 and 18, were selected for in vivo studies in rats, and compared to propranolol, a well-accepted standard for β-blockers. In the first set of experiments, the compounds were administered intraperitoneally at 6 mg/kg dose, and blood pressure and heart rate were monitored. One hour after administration of the blocker, an agonist, isoproterenol, was given and the changes in heart rate and blood pressure were recorded continuously. The main purpose of these experiments was to determine if the compounds show any activity at all 60 minutes after administration, considering their very short plasma half-lives. The results shown in FIG. 1 indicate that the esters 17 and 13 effectively control the heart rate, although their in vitro plasma half-life is on the order of 1 minute. (In vivo hydrolysis rates cannot be measured accurately since the drugs were administered i.p. and the in vitro half-life is very short.) The extent of this activity if of particular interest, and the time dependence was determined in the case of 17. Following administration of 17, as before, the isoproterenol was administered 15, 60 and 90 minutes later and the blood pressure and heart rates were recorded. It appears from FIG. 2 that at 15 and 60 minutes there is significant activity on heart rate which, however, disappears at 90 minutes. FIG. 3 indicates minimal effect on the blood pressure.

Additional in vivo cardiovascular experiments were performed, using dogs, which are good models for these types of experiments. In order to avoid the uncertainty due to the intraperitoneal administration used for rats, the active compounds were administered i.v. The changes in heart rate and in left ventricular pressure (LVP) were monitored, as the effect of isoproterenol was antagonized. Based on the selected lead compound, the tetramethylcyclohexyl ester 17, the simpler homologues 15 and 16 were tested and compared to the simple ethyl ester, 10. All four compounds showed β1-antagonist activity, but the cyclohexyl ester 15 was the most potent in blocking the cardiac effects of isoproterenol. The other three agents had a comparable ability to block isoproterenol-induced tachycardia; see FIG. 4.

The time course of the β-adrenergic blockage on heart rate differed among the four compounds. While 10 produced an antagonism which dissipated fairly consistently between 45 and 60 minutes after administration, the duration of action of 16 and 17 was much more variable and generally longer It is interesting to note that just as in rats (FIG. 2, compound 17), in dogs the maximum blockade was not at the earliest time following administration, but at 45 or 60 minutes (TABLE III). Compound 15 had the longest duration of action; approximately 90 minutes were required in most cases for return of heart rate responsiveness to isoproterenol to the control value (TABLE III).

All compounds shifted the dose-response curve of isoproterenol on left ventricular contractility (dP/dt) to the right. While the extent of this inotropic blockade may be less than the chronotropic (HR) blockade, the inotropic blockade was more variable. None of the agents were found to have any significant effect upon the diastolic depressor response to isoproterenol.

Thus, ester type "soft" β-blockers of the present invention based on an acidic inactive metabolite of metoprolol have been shown to possess significant β-blocking activity and the duration of action do not show any correlation with the in vitro plasma hydrolysis rates. To the contrary, the longest acting compound, 15, has the shortest plasma hydrolytic half-life (<1 min). The fast, predictable hydrolytic deactivation of the circulating active species must result in reduced overall toxicity and the indirect drug interaction. In view of the structure of known metabolites of metoprolol, it is unlikely that oxidative metabolism would compete with the hydrolysis of the soft derivatives.

EXAMPLE 25

The following illustrates the preparation of an injectable solution containing a representative compound of the invention.

| Ingredient | Amount |
|---|---|
| Cyclohexyl 4-(2-hydroxy-3-isopropylamino)-propoxyphenylacetate oxalate ¼ hydrate | 500 mg |
| Polyethylene glycol (molecular weight 4000) | 0.3 g |
| Sodium chloride | 0.9 g |
| Polyoxyethylene sorbitan monooleate | 0.4 g |
| Sodium metabisulfite | 0.1 g |
| Methyl paraben | 0.18 g |
| Propyl paraben | 0.02 g |
| Distilled water for injection | 100 mL |

The parabens, sodium metabisulfite and sodium chloride are dissolved in distilled water with stirring at 80° C. The solution is cooled to 40° C., then to this solution are added the compound of the present invention, polyethylene glycol and polyoxyethylene sorbitan monooleate, successively. To this solution is added distilled water for injection to the desired volume, and the solution is then sterilized by filtering through a suitable filter paper. One mL portions of this sterilized solution are introduced into ampoules.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A compound of the formula

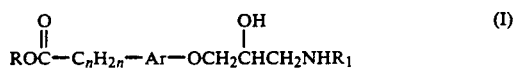

or a pharmaceutically acceptable acid addition salt thereof, wherein:

n is an integer from 0 to 10 inclusive;

R is

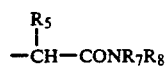

wherein $R_5$ is hydrogen or $C_1$-$C_7$ alkyl and $R_7$ and $R_8$, which can be the same or different, are each hydrogen, $C_1$-$C_7$ alkyl, $C_3$-$C_{12}$ cycloalkyl, phenyl or benzyl, or $R_7$ and $R_8$ are combined such that —$NR_7R_8$ represents the residue of a saturated monocyclic secondary amine having 5 to 7 ring atoms, optionally having another hetero atom, which can be —O—, —S— or —N—, in addition to the indicated nitrogen atom, and optionally bearing one or more phenyl, benzyl or methyl substituents;

$R_1$ is $C_1$-$C_7$ alkyl;

and Ar is a divalent radical selected from the group consisting of:

(a) unsubstituted phenylene; and (b) phenylene substituted by $C_1$-$C_7$ alkyl, $C_1$-$C_7$ alkyl—O—$C_1$-$C_7$ alkylene-, $C_2$-$C_8$ alkenyl, $C_2$-$C_8$ alkenyl—O—, $C_{13}$-$C_{12}$ cycloalkyl, $C_1$-$C_7$-alkyl—CONH—, $C_1$-$C_7$ alkyl—CO— or $H_2NCO$—$C_1$-$C_7$ alkylene-.

2. The compound as defined by claim 1, wherein n is zero, one or two.

3. The compound as defined by claim 1, wherein $R_7$ and $R_8$, which can be the same or different, are each hydrogen, $C_1$-$C_7$ alkyl, $C_3$-$C_{12}$ cycloalkyl, phenyl or benzyl, or $R_7$ and $R_8$ are combined such that —$NR_7R_8$ is morpholino, 1-pyrrolidinyl, 4-benzyl-1-piperazinyl, perhydro-1,2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino or 4-phenyl-1-piperazinyl.

4. The compound as defined by claim 3, wherein $R_7$ is hydrogen and $R_8$ is hydrogen.

5. The compound as defined by claim 4, wherein R is carbamoylmethyl.

6. The compound as defined by claim 1, wherein Ar is a divalent radical selected from the group consisting of:

(a) unsubstituted 1,4- or 1,3-phenylene; and (b) phenylene substituted by a $CH_3CH_2$—, $CH_3$—, $CH_3OCH_2CH_2$—, $CH_2=CH$—$CH_2$—, $CH_2CH=CH_2$—O—,

$CH_3CH_2CH_2CONH-$, $CH_3CONH-$, $CH_3CO-$ or $H_2NCO-CH_2-$.

7. The compound as defined by claim 1, wherein Ar is unsubstituted phenylene.

8. The compound as defined by claim 7, wherein Ar is 1,4-phenylene or 1,3-phenylene.

9. The compound as defined by claim 1, wherein $R_1$ is isopropyl or tert-butyl.

10. The oxalate salt of a compound as defined by claim 1.

11. Carbamoylmethyl 4-(2-hydroxy-3-isopropylamino)propoxyphenylacetate or a pharmaceutically acceptable acid addition salt thereof.

12. The oxalate salt of carbamoylmethyl 4-(2-hydroxy-3-isopropylamino)propoxyphenylacetate.

13. A method for eliciting a β-adrenergic blocking response in a warm-blooded animal, which comprises administering to said animal an effective β-adrenergic blocking amount of a compound of formula (I) as defined by claim 1, or a pharmaceutically acceptable acid addition salt thereof.

14. A pharmaceutical composition of matter, in unit dosage form, for use in eliciting a β-adrenergic blocking response in a warm-blooded animal, said composition comprising, per dosage unit, an effective unit β-adrenergic blocking amount of a compound of formula (I) as defined by claim 1 or a pharmaceutically acceptable acid addition salt thereof, and a non-toxic pharmaceutically acceptable carrier therefor.

15. A method for the treatment of glaucoma or for lowering intraocular pressure in a warm-blooded animal, which comprises administering to the eye or the eyes of said animal an effective intraocular pressure decreasing amount of a compound of formula (I) as defined by claim 1, or a pharmaceutically acceptable acid addition salt thereof.

16. An ophthalmic composition of matter, in unit dosage form, for use in the treatment of glaucoma or in the lowering of intraocular pressure in a warm-blooded animal, said composition comprising, per dosage unit, an effective unit intraocular pressure decreasing amount of a compound of formula (I) as defined by claim 1 or a pharmaceutically acceptable acid addition salt thereof, and a non-toxic ophthalmically acceptable carrier therefor.

* * * * *